US010407669B2

(12) United States Patent
Mazaleyrat et al.

(10) Patent No.: US 10,407,669 B2
(45) Date of Patent: Sep. 10, 2019

(54) HIV KINASE VARIANTS

(71) Applicants: Global Bioenergies, Evry (FR); Scientist of Fortune, S.A., Luxembourg (LU)

(72) Inventors: Sabine Mazaleyrat, Le Russey (FR); Jean-Baptiste Barbaroux, Marseilles (FR); Marc Delcourt, Paris (FR); Francois Stricher, Wolfsheim (FR); Philippe Marlière, Tournai (BE)

(73) Assignees: Global Bioenergies, Evry (FR); Scientist of Fortune, S.A., Luxembourg (LU)

( * ) Notice: Subject to any disclaimer, the term of this patent is extended or adjusted under 35 U.S.C. 154(b) by 0 days.

(21) Appl. No.: 15/748,034

(22) PCT Filed: Jul. 27, 2016

(86) PCT No.: PCT/EP2016/067865

§ 371 (c)(1),
(2) Date: Jan. 26, 2018

(87) PCT Pub. No.: WO2017/017124

PCT Pub. Date: Feb. 2, 2017

(65) Prior Publication Data

US 2018/0223266 A1 Aug. 9, 2018

(30) Foreign Application Priority Data

Jul. 28, 2015 (EP) .................................... 15178677

(51) Int. Cl.

| | |
|---|---|
| ***C12N 9/12*** | (2006.01) |
| ***C12P 9/00*** | (2006.01) |
| ***C07C 11/09*** | (2006.01) |
| ***C12P 5/02*** | (2006.01) |
| ***C12N 9/88*** | (2006.01) |

(52) U.S. Cl.

CPC ................ *C12N 9/12* (2013.01); *C07C 11/09* (2013.01); *C12N 9/88* (2013.01); *C12P 5/026* (2013.01); *C12P 9/00* (2013.01); *C12Y 401/01033* (2013.01)

(58) Field of Classification Search

CPC . C07C 11/09; C12P 5/026; C12P 5/02; C12N 9/12; C12N 9/88; C12Y 401/01033

See application file for complete search history.

(56) References Cited

U.S. PATENT DOCUMENTS 9,193,978 B2 * 11/2015 Delcourt .................. C12N 9/88

FOREIGN PATENT DOCUMENTS

| | | | | |
|---|---|---|---|---|
| WO | 2012052427 A1 | 4/2012 | | |
| WO | 2013092567 A2 | 6/2013 | | |
| WO | WO-2015004211 A2 * | 1/2015 | ..... | C12Y 401/01033 |
| WO | 2015101493 A1 | 7/2015 | | |

OTHER PUBLICATIONS

Broun et al., Catalytic plasticity of fatty acid modification enzymes underlying chemical diversity of plant lipids. Science, 1998, vol. 282: 1315-1317. (Year: 1998).*

Chica et al., Semi-rational approaches to engineering enzyme activity: combining the benefits of directed evolution and rational design. Curr. Opi. Biotechnol., 2005, vol. 16: 378-384. (Year: 2005).*

Devos et al., Practical limits of function prediction. Proteins: Structure, Function, and Genetics. 2000, vol. 41: 98-107. (Year: 2000).*

Seffernick et al., Melamine deaminase and Atrazine chlorohydrolase: 98 percent identical but functionally different. J. Bacteriol., 2001, vol. 183 (8): 2405-2410. (Year: 2001).*

Sen et al., Developments in directed evolution for improving enzyme functions. Appl. Biochem. Biotechnol., 2007, vol. 143: 212-223. (Year: 2007).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Guo et al., Protein tolerance to random amino acid change. PNAS., 2004, vol. 101 (25): 9205-9210. (Year: 2004).*

International Preliminary Report on Patentability dated Feb. 8, 2018 and received in PCT/EP2016/067865.

European Search Report dated Oct. 23, 2015 and received in 15178677.9.

International Search Report and Written Opinion dated Oct. 18, 2016 in PCT/EP2016/067865.

Vinokur, et. al, "Evidence of a Novel Mevalonate Pathway in Archaea", Biochemistry, vol. 53, Jun. 10, 2014, pp. 4161-4168 (XP55134842).

Vinokur, et. al., "Structural Analysis of Mevalonate-3-Kinase Provides Insight Into the Mechanisms of Isoprenoid Patheway Decarboxylases", The Protein Society, vol. 24, Nov. 25, 2014, pp. 212-220 (XP002745804).

* cited by examiner

*Primary Examiner* — Ganapathirama Raghu

(74) *Attorney, Agent, or Firm* — Michele M. Wales; Inhouse Patent Counsel, LLC

(57) ABSTRACT

Described are HIV kinase variants showing an improved activity in converting 3-hydroxyisovalerate (HIV) into 3-phosphonoxyisovalerate (PIV), methods for the production of PIV using such enzyme variants as well as methods for the production isobutene in a subsequent reaction.

19 Claims, 2 Drawing Sheets

Figure 1:
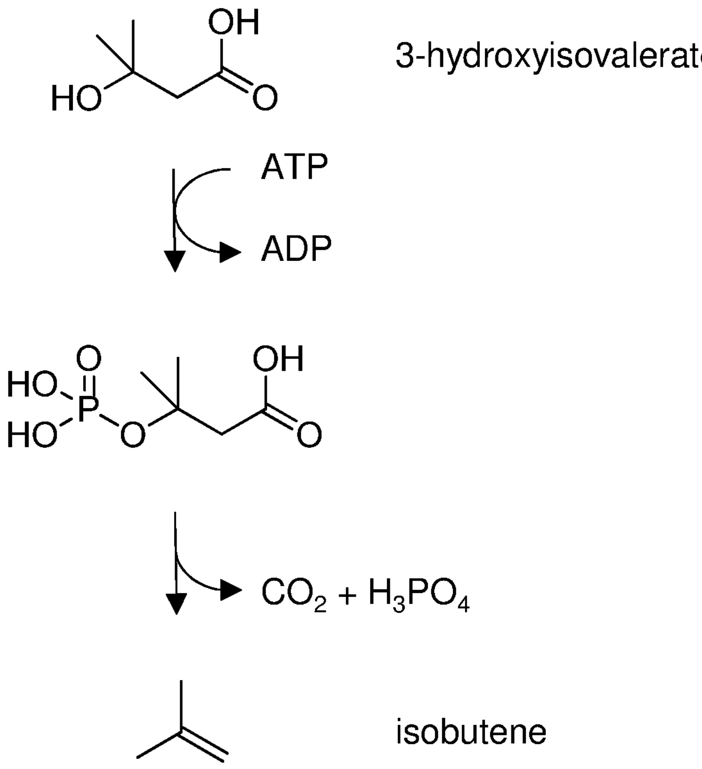

Specification includes a Sequence Listing.

3-hydroxyisovalerate isobutene

| | Et (M) | kcat (s-1) | Km (M) | Vmax (M.s-1) | kcat/Km |
|---|---|---|---|---|---|
| L200E | 2.86E-06 | 5.46E-01 | 1.03E-02 | 1.56E-06 | 5.30E+01 |
| L200E-C43S-V74P-R80A-Y81R-N133S-S141G-R197L-H211R-K303T-R307H | 2.86E-06 | 2.10 | 1.27E-02 | 6.02E-06 | 1.65E+02 |

SEQUENCE LISTING

```
<160> NUMBER OF SEQ ID NOS: 1

<210> SEQ ID NO 1
<211> LENGTH: 318
<212> TYPE: PRT
<213> ORGANISM: Thermoplasma acidophilum

<400> SEQUENCE: 1

Met Thr Tyr Arg Ser Ile Gly Ser Thr Ala Tyr Pro Thr Ile Gly Val
1               5                   10                  15

Val Leu Leu Gly Gly Ile Ala Asn Pro Val Thr Arg Thr Pro Leu His
            20                  25                  30

Thr Ser Ala Gly Ile Ala Tyr Ser Asp Ser Cys Gly Ser Ile Arg Ser
        35                  40                  45

Glu Thr Arg Ile Tyr Ala Asp Glu Ala Thr His Ile Tyr Phe Asn Gly
    50                  55                  60

Thr Glu Ser Thr Asp Asp Asn Arg Ser Val Arg Arg Val Leu Asp Arg
65                  70                  75                  80

Tyr Ser Ser Val Phe Glu Glu Ala Phe Gly Thr Lys Thr Val Ser Tyr
                85                  90                  95

Ser Ser Gln Asn Phe Gly Ile Leu Ser Gly Ser Ser Asp Ala Gly Ala
            100                 105                 110

Ala Ser Ile Gly Ala Ala Ile Leu Gly Leu Lys Pro Asp Leu Asp Pro
        115                 120                 125

His Asp Val Glu Asn Asp Leu Arg Ala Val Ser Glu Ser Ala Gly Arg
    130                 135                 140

Ser Leu Phe Gly Gly Leu Thr Ile Thr Trp Ser Asp Gly Phe His Ala
145                 150                 155                 160

Tyr Thr Glu Lys Ile Leu Asp Pro Glu Ala Phe Ser Gly Tyr Ser Ile
                165                 170                 175

Val Ala Phe Ala Phe Asp Tyr Gln Arg Asn Pro Ser Asp Val Ile His
            180                 185                 190

Gln Asn Ile Val Arg Ser Asp Leu Tyr Pro Ala Arg Lys Lys His Ala
        195                 200                 205

Asp Glu His Ala His Met Ile Lys Glu Tyr Ala Lys Thr Asn Asp Ile
    210                 215                 220
```

-continued

```
Lys Gly Ile Phe Asp Leu Ala Gln Glu Asp Thr Glu Glu Tyr His Ser
225                 230                 235                 240

Ile Leu Arg Gly Val Gly Val Asn Val Ile Arg Glu Asn Met Gln Lys
                245                 250                 255

Leu Ile Ser Tyr Leu Lys Leu Ile Arg Lys Asp Tyr Trp Asn Ala Tyr
            260                 265                 270

Ile Val Thr Gly Gly Ser Asn Val Tyr Val Ala Val Glu Ser Glu Asn
        275                 280                 285

Ala Asp Arg Leu Phe Ser Ile Glu Asn Thr Phe Gly Ser Lys Lys Lys
    290                 295                 300

Met Leu Arg Ile Val Gly Gly Ala Trp His Arg Arg Pro Glu
305                 310                 315
```

HIV KINASE VARIANTS

CROSS-REFERENCE TO RELATED APPLICATIONS

This application is a § 371 National Stage Application of PCT/EP2016/067865filed on Jul. 27, 2016, which claims priority to EP Provisional Application 15178677.9 filed on Jul. 28, 2015. All of these documents are hereby incorporated by reference in their entirety.

The present invention relates to HIV kinase variants showing an improved activity in converting 3-hydroxyisovalerate (HIV) into 3-phosphonoxyisovalerate (PIV), methods for the production of PIV using such enzyme variants as well as methods for the production isobutene in a subsequent reaction.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels. Over the past years, the bioproduction of plastics ("bioplastics") and biofuels has become a thriving field due to economic concerns linked to the price of oil, and to environmental considerations that are both global (carbon-neutral products) and local (waste management). Thus, there is a need for efficient enzymes for producing alkenes such as isobutene.

WO 2010/001078 describes a process for producing alkenes, such as isobutene, by enzymatic conversion of 3-hydroxyalkanoic acids with an enzyme having the activity of a decarboxylase, for example a mevalonate diphosphate (MDP) decarboxylase. Such a method is advantageous because it helps to avoid the use of petroleum products, to lower the costs of producing plastics and fuels and can have a considerable global environmental impact by allowing carbon to be stored in solid form. It could be shown that mevalonate diphosphate decarboxylase is capable of using substrates other than its natural substrate mevalonate diphosphate, in particular 3-hydroxyalkanoic acids, and convert them into terminal alkenes. Mevalonate diphosphate (MDP) decarboxylase (enzyme nomenclature EC 4.1.1.33) is an enzyme involved in cholesterol biosynthesis.

WO 2010/001078 discloses, inter alia, that it is possible to convert 3-hydroxy-3-methylbutyrate (or 3-hydroxyisovalerate (HIV)) into isobutene by a decarboxylase, in particular an MDP decarboxylase. In this case, the reaction intermediate is 3-phosphonoxyisovalerate (PIV) which is further converted in the second part of the reaction into isobutene. Gogerty et al. (Appl. Environ. Microbiol. 76 (2010), 8004-8010) also report on the formation of isobutene from 3-hydroxy-3-methylbutyrate using an MDP decarboxylase from *S. cerevisiae* and show that mutations at residues 145 and 74 of this enzyme, which are located within or close to the proposed active site of this enzyme, lead to an increase of the conversion of 3-hydroxy-3-methylbutyrate into isobutene. However, the level of production of isobutene achieved is still too low for commercial application.

Later works have shown that different enzymes, in particular MDP decarboxylases, may show different efficiencies as regards the catalysis of the first and the second step of the reaction as described above, with some enzymes showing a high activity in the first step and others showing a high activity in the second step. Therefore, it had been proposed to combine two enzymes which show a high activity in the first and in the second step of the reaction, respectively, so as to optimize the overall enzymatic reaction (WO2012/052427).

Thus, an artificial metabolic pathway for the production of isobutene from 3-hydroxy-3-methylbutyric acid (also referred to as beta-hydroxyisovalerate, 3-hydroxyisovalerate or HIV) has previously been described wherein HIV is decarboxylated into isobutene in a two-step pathway as described in FIG. 1. In a first step, HIV is activated by an ATP-dependent phosphorylation resulting in 3-phosphonoxyisovalerate (PIV). In a second step, PIV is decarboxylated into isobutene.

Moreover, the production of HIV from acetone has previously been described wherein, in a condensation reaction, acetone and acetyl-CoA are reacted by an HMG-CoA synthase to form HIV (WO2011/032934). Further, variants derived from the *Mus musculus* HMG-CoA synthase have been described having improved capabilities in condensing acetone and acetyl-CoA into HIV (WO2015/101493). The HIV produced from acetone and acetyl-CoA (catalyzed by either an HMG-CoA synthase or a variant thereof) may then form the starting molecule for the above two step reaction, i.e., the activation by an ATP-dependent phosphorylation resulting in 3-phosphonoxyisovalerate (PIV) which, in a second step, is decarboxylated into isobutene.

With respect to this second step, previously, mevalonate diphosphate (MDP) decarboxylase variants having improved activity in converting 3-phosphonoxyisovalerate into isobutene have been described (WO2015/004211). With respect to the first step of the reaction, it has previously been described that, inter alia, the *Thermoplasma acidophilum* mevalonate kinase (SEQ ID NO:1) is capable of catalyzing, amongst other reactions, the phosphorylation of HIV into 3-phosphonoxyisovalerate (PIV). However, with respect to this first step of the reaction, no enzyme variants are known having an improved activity in converting HIV into PIV.

Therefore, although the above means and methods allow to produce isobutene (IBN) from 3-hydroxyisovalerate (HIV), there is still a need for improvements, in particular as regards a further increase in efficiency of the process so as to make it more suitable for industrial purposes, in particular regarding the first step of the above reaction, i.e., the conversion of HIV into 3-phosphonoxyisovalerate (PIV).

The present application addresses this need by providing the embodiments as defined in the claims.

Thus, the present invention provides a variant of an HIV kinase showing an improved activity in converting 3-hydroxyisovalerate (HIV) into 3-phosphonoxyisovalerate (PIV) over the corresponding HIV kinase from which it is derived, wherein the HIV kinase variant is characterized in that it shows one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

In the context of the present invention, an "improved activity" means that the activity of the enzyme in question is at least 10%, preferably at least 20%, more preferably at least 30% or 50%, even more preferably at least 70% or 80% and particularly preferred at least 90% or 100% higher than that of the enzyme from which the variant is derived, preferably higher than that the enzyme represented by SEQ ID NO:1. In even more preferred embodiments the improved activity may be at least 150%, at least 200%, at least 300%, at least 750% or at least 1000% higher than that of the corresponding enzyme from which the variant is derived, preferably higher than that of the enzyme represented by SEQ ID NO:1. In a particularly preferred embodiment, the activity is measured by using an assay with purified enzyme and chemically synthesized substrates, as described below. The improved activity of a variant can be measured as a higher PIV production in a given time under defined conditions, compared with the parent enzyme. This improved activity can result from a higher turnover number, e.g. a higher kcat value. It can also result from a lower Km value. It can also result from a higher kcat/Km value. Finally, it can result from a higher solubility, or stability of the enzyme. The degree of improvement can be measured as the improvement in 3-phosphonoxyisovalerate (PIV) production. The degree of improvement can also be measured in terms of kcat improvement, of kcat/Km improvement, or in terms of Km decrease, or in terms of soluble protein production.

The enzyme variants which the present invention provides are capable of converting HIV into PIV with an activity which is at least 1.25 times as high compared to the turnover rate of the corresponding wild type enzyme having the amino acid sequence as shown in SEQ ID NO:1. In a more preferred embodiment, the enzyme variants which are capable of converting HIV into PIV have a turnover rate (i.e., a $K_{cat}$-value) which is at least 2 times, at least 3 times, at least 5 times or even at least 10 times as high compared to the turnover rate of the corresponding wild type enzyme having the amino acid sequence as shown in SEQ ID NO:1. In even more preferred embodiments, the turnover rate is at least 100 times or even at least 500 times as high compared to that of the corresponding wild type enzyme having the amino acid sequence as shown in SEQ ID NO:1.

Such enzyme variants are obtained by effecting mutations at specific positions in an HIV kinase and the variants obtained by effecting such mutations show an improved activity in catalyzing the conversion of HIV into PIV. The turnover rate of an enzyme capable of converting HIV into PIV may be determined by methods known to the person skilled in the art. In one embodiment, this turnover rate is determined as described in the Examples appended hereto. In a particular embodiment this turnover rate can be measured by incubating the enzyme, preferably a cell lysate containing the overexpressed recombinant protein, in vitro. Alternatively, a purified enzyme can be used.

More specifically, the activity of the HIV kinase variants for the conversion of 3-hydroxyisovalerate (HIV) into 3-phosphonoxyisovalerate (PIV) can be assessed by an enzymatic in vitro assay based on purified proteins and on the detection of PIV by High-Performance Liquid Chromatography (HPLC). The turnover rate of the enzyme to be assessed may be examined as outlined in the following: Michaelis-Menten $k_{cat}$ and $K_m$ steady state kinetic constants for the reaction of conversion of HIV into PIV may be determined using the following protocol:

The enzymatic assay for quantifying the conversion of HIV into PIV is carried out at 37° C. in a 50 mM Tris/HCl pH 7.5 buffer with 10 mM MgCl2, 10 mM NaCl, 20 mM ATP, 0.1 mg/mL enzyme and different concentrations of HIV ranging from 0 to 128 mM. After 30 min, the reaction is stopped by incubating at 80° C. for 5 min. The rate of PIV production is quantified by HPLC analysis performed using a 1260 Infinity LC System (Agilent), equipped with a refractometer detector and a column heating module. 2 μL sample is separated on a Polaris 150 column (150×2 mm, 5 μm particle size, column temperature 30° C.). The mobile phase consists of 16 mM sulphuric acid in water with 1% methanol and is run with a flow rate of 1.5 mL/min. Retention time of HIV and PIV under these conditions is 4.8 and 3.5 min, respectively. Commercial HIV and PIV is used as reference. From the rate of PIV production, and using the Michaelis-Menten approximation, the enzyme catalytic efficiency can then be computed. The production rates of PIV (mole of PV/mole enzyme/sec) are plotted as a function of the concentration of HIV and the curve is fitted using the Michaelis Menten equation ($V=(V_{max}*(\text{substrate}))/(K_m+(\text{substrate}))$) to extract the $k_{cat}$ ($s^{-1}$) and the Km values (mM).

Alternatively, Michaelis-Menten $k_{cat}$ and $K_m$ steady state kinetic constants for the reaction of conversion of HIV into PIV may be determined using the following protocol:

The conversion of HIV into PIV is accompanied by a dephosphorylation of ATP into ADP, i.e., a conversion of ATP into ADP. It is thus possible to follow the rate of conversion of HIV into PIV by measuring the production of ADP, by assays known to the person skilled in the art. The release of ADP can, e.g., be quantified using a pyruvate kinase/lactate dehydrogenase coupled assay. Briefly, in the presence of ADP and the pyruvate kinase (PK), phosphoenolpyruvate (PEP) is converted into pyruvate, which is then converted into lactate by the lactate dehydrogenase (LDH). This last reaction requires a molecule of NADH which is oxidised in $NAD_+$. The rate of NADH oxidation, proportional to the ADP production, is followed by the rate of absorbance decrease at 340 nm. The enzymatic reaction is carried out at 40° C. in a 50 mM Tris-HCl pH7 buffer, with 10 mM MgCl2, 100 mM KCl, 0.4 mM NADH, 1 mM PEP, 1.5 U/mL PK and 3 U/mL LDH, 5 mM ATP, the mevalonate kinase variant at 0.05 mg/mL and different concentrations of HIV ranging from 0 to 20 mM. By following the absorbance at 340 nm, an initial velocity of conversion can be calculated and using the Michaelis-Menten approximation, the enzyme catalytic efficiency can be computed.

The HIV kinase variant to be tested can be provided according to the following protocol: The HIV kinase to be tested is sub-cloned into the commercial pET 25b vector (Novagen). A stretch of 6 histidine codons is inserted after the methionine initiation codon to provide an affinity tag for purification and a unique cleavage site for the TEV protease (ENLYFQG) in order to remove the affinity tag from the purified protein. Competent *E. coli* BL21 (DE3) cells (Novagen) are transformed with these vectors according to the heat shock procedure and plated out onto LB-agar plates supplemented with the appropriate antibiotic. Cells are grown overnight at 30° C. until individual colonies reach the desired size. Single colonies are then picked and individually transferred into 5 mL of liquid LB medium supplemented with the appropriate antibiotic. Cell growth is carried out with shaking for 16 hours at 30° C. The LB cultures are used to inoculate 1 L of auto-induction medium (Studier F W, Prat. Exp. Pur. 41, (2005), 207-234) supplemented with the appropriate antibiotic and grown in a shaking incubator set at 170 rpm and 85% humidity for 6 h at 37° C. and protein expression is continued at 28° C. overnight (approximately 16 h). The cells are collected by centrifugation at 4° C., 4000 rpm for 20 min and the pellets were frozen at −80° C. The pellets are thawed on ice and resuspended in 40 ml of BugBuster (Millipore) and four microliter of lysonase (Novagen) is added. Cells are incubated 10 minutes at room temperature and then returned to ice for 20 minutes. The bacterial extracts are then clarified by centrifugation at 4° C., 10,000 rpm for 30 min. The clarified bacterial lysates are loaded on Protino Ni-IDA columns (Macherey-Nagel) allowing adsorption of 6-His tagged proteins. Columns are washed and the enzymes of interest are eluted with 6 mL of the supplied elution buffer. Eluates are then concentrated and desalted by centrifugation, washing and resuspension in 1 mL of 100 mM Tris/HCl pH 7.5, 50 mM NaCl, 5% glycerol. Protein concentrations are quantified using a Nanodrop 1000 (ThermoScientific). Cleavage of the affinity tag is then performed by adding 100 U TEV protease (Invitrogen) per 1 μg of purified protein and incubated overnight at 4° C. The uncleaved proteins are separated by affinity chromatography using an Akta Purifier and a HisTrap HP 5 mL column (GE Healthcare Life Sciences) using standard protocol. The cleaved proteins are collected in the flow-through and concentrated by centrifugation, washing and resuspension in 100 μL of 50 mM Tris/HCl pH 7.5 on Amicon Ultra 4 mL with a 10 kDa cut-off (Merck Millipore). Protein concentrations are quantified using a Nanodrop 1000 (ThermoScientific).

Alternatively to the above in vitro assays, the activity of the HIV kinase variants for the conversion of 3-hydroxyisovalerate (HIV) into 3-phosphonoxyisovalerate (PIV) can be assessed by an in vivo testing. This coupled in vivo assay is based on the use of a bacterial strain transformed with an expression vector that contains the coding sequences leading to the production of three enzymes involved in a three-step metabolic pathway converting acetone to isobutene. In this pathway, the first step is the production of 3-hydroxyisovalerate (HIV) from acetone. The condensation of acetone and acetyl-CoA into 3-hydroxyisovalerate by HMG-CoA synthases has been described previously (WO2011032934). Variants of the *Mus musculus* HMG-CoA Synthase (referred to in the following as "HIV synthase") may be used which have previously been described in WO2015/101493. Thus, in the coupled in vivo assay, a bacterial strain is used which is transformed with an expression vector that contains the coding sequence of an HIV synthase or a variant thereof. In this assay, acetone is exogenously provided while acetyl-CoA is provided by the *E. coli* strain. The second step is the phosphorylation of HIV into PIV. The mevalonate kinase/HIV kinase variant of the present invention to be tested is used to catalyze this step. Thus, in the coupled in vivo assay, a bacterial strain is used which is transformed with an expression vector that contains the coding sequence of a mevalonate kinase/HIV kinase variant which is to be tested. The third step is the decarboxylation of 3-phosphonoxyisovalerate into isobutene (IBN), catalyzed by a mevaonate diphosphate decarboxylase, as described in WO2012052427. Variants of the *Streptococcus mitis* MDP decarboxylase (referred to in the following as PIV decarboxylase), described in WO2015004211, may be used. Thus, in the coupled in vivo assay, a bacterial strain is used which is transformed with an expression vector that contains the coding sequence of a mevaonate diphosphate decarboxylase or a variant thereof, preferably a *Streptococcus mitis* MDP decarboxylase variant. The transformed strain is first plated out onto LB-agar plates supplemented with the appropriate antibiotic. Cells are then grown overnight at 30° C. until individual colonies reach the desired size. Single colonies are then picked and individually transferred into either 50 or 500 μL of liquid LB medium supplemented with the appropriate antibiotic. Cell growth is carried out with shaking for 20 hours at 30° C. The LB cultures are used to inoculate 300 μL in 384 deepwell microplates or 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the three types of recombinant enzymes. The cell pellet containing these three overexpressed recombinant enzymes is then resuspended in 50 μL (or 500 μL) of minimum medium supplemented with 250 mM or 500 mM acetone and incubated for a further 16 hours in a shaking incubator at 37° C., 700 rpm. During this step, HIV synthase catalyzes the condensation of acetone with the cellular acetyl-CoA into HIV, which is then converted into PIV by the mevalonate kinase/HIV kinase variant to be tested. The PIV decarboxylase finally catalyzes the conversion of PIV into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples are separated by chromatography using a RTX-1 columns at 100° C. with a 1 mL/min constant flow of nitrogen as carrier gas. Upon injection, peak areas of isobutene are calculated.

Alternatively to the above in vivo assay, the activity of the HIV kinase variants for the conversion of 3-hydroxyisovalerate (HIV) into 3-phosphonoxyisovalerate (PIV) can be assessed by another in vivo testing as described in the following:

This assay is based on the use of a bacterial strain transformed with an expression vector that contain the coding sequences leading to the production of the last two enzymes involved in a metabolic pathway converting HIV to isobutene. The reactions involved in this pathway are the two last reactions of the pathway used in the above-described first in vivo assay: phosphorylation of HIV into PIV and decarboxylation of PIV into isobutene. The same enzymes may be used as for the above-described first assay. Thus, in this in vivo assay, a bacterial strain is used which is transformed with an expression vector that contains the coding sequence of a mevalonate kinase/HIV kinase variant which is to be tested. Moreover, this bacterial strain is transformed with an expression vector that contains the coding sequence of a mevaonate diphosphate decarboxylase or a variant thereof, preferably a *Streptococcus mitis* MDP decarboxylase variant.

This strain is first plated out onto LB-agar plates supplemented with the appropriate antibiotic. Cells are then grown overnight at 30° C. until individual colonies reach the desired size. Single colonies are then picked and individually transferred into 50 of liquid LB medium supplemented with the appropriate antibiotic. Cell growth is carried out with shaking for 20 hours at 30° C. The LB cultures are used to inoculate 300 μL in 384 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the two types of recombinant enzymes. The cell pellet containing these two overexpressed recombinant enzymes is then resuspended in 30 μL of minimum medium supplemented with 10 mM HIV and incubated for a further 4 or 16 hours in a shaking incubator at 37° C., 700 rpm. During this step, the mevalonate kinase/HIV kinase variant to be tested catalyzes the phosphorylation of HIV into PIV. The PIV decarboxylase finally catalyzes the conversion of PIV into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples are separated by chromatography using a RTX-1 columns at 100° C. with a 1 mL/min constant flow of nitrogen as carrier gas. Upon injection, peak areas of isobutene are calculated.

By providing the above described enzyme variant, the present invention allows to dramatically increase the production efficiency of PIV from HIV.

The term "HIV kinase" refers to an enzyme which can catalyze the transfer of a phosphate group from a high-energy, phosphate-donating molecule (e.g., ATP) to the substrate HIV. This transfer of a phosphate group is known as phosphorylation when the substrate gains a phosphate group and the high energy molecule, e.g., ATP, donates a phosphate group, thereby producing a phosphorylated substrate and a high energy molecule devoid of one phosphate group, e.g., ADP. This activity can be measured by methods known in the art. In a preferred embodiment, the HIV kinase is a mevalonate kinase. The term "mevalonate kinase" in the context of the present invention refers to an enzyme which is capable of converting mevalonate into mevalonate phosphate by a phosphorylation reaction. Preferably, this reaction is ATP-dependent, i.e., the phosphorylation occurs by the transfer of a phosphate group from ATP to mevalonate and the concomitant generation of ADP.

Even more preferably, such a mevalonate kinase is a mevalonate-3-kinase, i.e., a kinase which catalyzes the phosphorylation of mevalonate to mevalonate-3-phosphate. The occurrence of a mevalonate-3-kinase has, e.g., been described for *Thermoplasma acidophilum* (Vinokur et al., Biochemistry 53(2014), 4161-4168; Azami et al., J. Biol. Chem. 289(2014), 15957-15967) where it constitutes a key enzyme of a recently discovered mevalonate pathway. A mevalonate-3-kinase has also been described to occur in *Picrophilus torridus* (Rossoni et al., Applied and Environmental Microbiology, 81(2015): 2625-2634). Rossoni et al. (loc. cit.) also shows that the mevalonate-3-kinase from *P. torridus* can convert HIV into PIV.

The present invention provides now improved variants of enzymes which are capable of converting HIV into PIV. The inventors used as a model enzyme the mevalonate kinase of *Thermoplasma acidophilum* shown in SEQ ID NO: 1 and could show that it is possible to provide variants of this enzyme which show increased activity with respect to the conversion of HIV into PIV.

The model enzyme, i.e., the mevalonate kinase of *Thermoplasma acidophilum,* as used by the inventors has the following amino acid sequence:

```
                                   (SEQ ID NO: 1)
MTYRSIGSTAYPTIGVVLLGGIANPVTRTPLHTSAGIAYSDSCGSIRSET

RIYADEATHIYFNGTESTDDNRSVRRVLDRYSSVFEEAFGTKTVSYSSQN

FGILSGSSDAGAASIGAAILGLKPDLDPHDVENDLRAVSESAGRSLFGGL

TITWSDGFHAYTEKILDPEAFSGYSIVAFAFDYQRNPSDVIHQNIVRSDL

YPARKKHADEHAHMIKEYAKTNDIKGIFDLAQEDTEEYHSILRGVGVNVI

RENMQKLISYLKLIRKDYWNAYIVTGGSNVYVAVESENADRLFSIENTFG

SKKKMLRIVGGAWHRRPE.
```

In one preferred embodiment the variants of the present invention are characterized by the feature that they are derived from an HIV kinase, more preferably a mevalonate kinase, even more preferably from a mevalonate-3-kinase and particularly preferred from a mevalonate-3-kinase having the amino acid sequence shown in SEQ ID NO:1 or a highly related sequence (at least 70% identical) and in which mutations are effected at one or more of the above indicated positions and by the feature that they show the ability to convert HIV into PIV and that they can do this with an improved activity. In a preferred embodiment the variant according to the present invention is derived from a sequence which shows at least 80% sequence identity to SEQ ID NO:1 and in which one or more substitutions and/or deletions and/or insertions at the positions indicated herein have been effected.

However, the teaching of the present invention is not restricted to the mevalonate kinase enzyme of *Thermoplasma acidophilum* shown in SEQ ID NO: 1 which had been used as a model enzyme but can be extended to mevalonate kinase enzymes from other organisms, in particular to other mevalonate-3-kinases, or to enzymes which are structurally related to SEQ ID NO:1 such as, e.g., truncated variants of the enzyme. Thus, the present invention also relates to variants of mevalonate kinases, preferably mevalonate-3-kinases, which are structurally related to the *Thermoplasma acidophilum* sequence (SEQ ID NO: 1) and which show one or more substitutions and/or deletions and/or insertions at positions corresponding to any of the positions as indicated herein. The term "structurally related" refers to mevalonate kinases, preferably mevalonate-3-kinases, which show a sequence identity of at least n % to the sequence shown in SEQ ID NO: 1 with n being an integer between 70 and 100, preferably 70, 71, 72, 73, 74, 75, 80, 85, 90, 91, 92, 93, 94, 95, 96, 97, 98 or 99. In a preferred embodiment the structurally related mevalonate kinase is of prokaryotic origin, even more preferably it stems from a bacterium, most preferably of a bacterium of the genus *Thermoplasma.*

Thus, in one embodiment, the variant of an HIV kinase according to the present invention has or preferably is derived from a sequence which is at least n % identical to SEQ ID NO:1 with n being an integer between 70 and 100, preferably 70, 71, 72, 73, 74, 75, 80, 85, 90, 91, 92, 93, 94, 95, 96, 97, 98 or 99, and it has (a) substitution(s) and/or (a) deletion and/or (an) insertion(s) at a position as indicated herein. When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 70% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open:

10; gap extension: 0.1. In the case of multiple comparisons/alignments, the following settings are preferably chosen: Protein weight matrix: BLOSUM 62; gap open: 10; gap extension: 0.2; gap distance: 5; no end gap. Preferably, the degree of identity is calculated over the complete length of the sequence.

Amino acid residues located at a position corresponding to a position as indicated herein in the amino acid sequence shown in SEQ ID NO:1 can be identified by the skilled person by methods known in the art. For example, such amino acid residues can be identified by aligning the sequence in question with the sequence shown in SEQ ID NO:1 and by identifying the positions which correspond to the above or below indicated positions of SEQ ID NO:1. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

When the amino acid sequences of HIV kinases are aligned by means of such a method, regardless of insertions or deletions that occur in the amino acid sequences, the positions of the corresponding amino acid residues can be determined in each of the HIV kinases.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagines etc.). Naturally occurring modifications also encompass the change in the chemical structure by citrullination, carbamylation and disulphide bond formation between cysteine residues; attachment of co-factors (FMN or FAD that can be covalently attached) or the attachement of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi: 101016/jchembio1.2009.03.001).

In the context of the present invention, "deleted" or "deletion" means that the amino acid at the corresponding position is deleted.

In the context of the present invention, "inserted" or "insertion" means that at the respective position one or two, preferably one amino acid residue is inserted, preferably in front of the indicated position.

The present invention relates in a preferred embodiment to an HIV kinase variant of having an amino acid sequence as shown in SEQ ID NO:1 or an amino acid sequence having at least 70% sequence identity to SEQ ID NO:1, in which one or more amino acid residues at a position selected from the group consisting of positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1 or at a position corresponding to any of these positions, are substituted with another amino acid residue or deleted or wherein an insertion has been effected at one or more of these positions and wherein said HIV kinase has an improved activity in converting HIV into PIV.

According to one embodiment, such an HIV kinase variant has an amino acid sequence as shown in SEQ ID NO:1 in which (1) an amino acid residue at position 3 in the amino acid sequence shown in SEQ ID NO:1 or at a position corresponding to this position, is deleted or substituted with histidine; and/or (2) an amino acid residue at position 5 in the amino acid sequence shown in SEQ ID NO:1 or at a position corresponding to this position, is deleted or substituted with alanine or phenylalanine; and/or (3) an amino acid residue at position 6 in the amino acid sequence shown in SEQ ID NO:1 or at a position corresponding to this position, is deleted or substituted with leucine; and/or (4) an amino acid residue at position 7 in the amino acid sequence shown in SEQ ID NO:1 or at a position corresponding to this position, is deleted or substituted with leucine, glutamine or valine; and/or (5) an amino acid residue at position 8 in the amino acid sequence shown in SEQ ID NO:1 or at a position corresponding to this position, is deleted or substituted with cysteine or threonine; and/or (6) an amino acid residue at position 9 in the amino acid sequence shown in SEQ ID NO:1 or at a position corresponding to this position, is deleted or substituted with histidine; and/or (7) an amino acid residue at position 14 in the amino acid sequence shown in SEQ ID NO:1 or at a position corresponding to this position, is deleted or substituted with valine; and/or (8) an amino acid residue at position 16 in the amino acid sequence shown in SEQ ID NO:1 or at a position corresponding to this position, is deleted or substituted with isoleucine; and/or (9) an amino acid residue at position 17 in the amino acid sequence shown in SEQ ID NO:1 or at a position corresponding to this position, is deleted or substituted with isoleucine or leucine; and/or

(10) an amino acid residue at position 23 in the amino acid sequence shown in SEQ ID NO:1 or at a position corresponding to this position, is deleted or substituted with threonine; and/or

(11) an amino acid residue at position 24 in the amino acid sequence shown in SEQ ID NO:1 or at a position corresponding to this position, is deleted or substituted with aspartic acid; and/or

(12) an amino acid residue at position 25 in the amino acid sequence shown in SEQ ID NO:1 or at a position corresponding to this position, is deleted or substituted with leucine, arginine or serine; and/or

(13) an amino acid residue at position 26 in the amino acid sequence shown in SEQ ID NO:1 or at a position corresponding to this position, is deleted or substituted with phenylalanine; and/or

(14) an amino acid residue at position 32 in the amino acid sequence shown in SEQ ID NO:1 or at a position corresponding to this position, is deleted or substituted with aspartic acid; and/or

(15) an amino acid residue at position 43 in the amino acid sequence shown in SEQ ID NO:1 or at a position corresponding to this position, is deleted or substituted with glycine or serine; and/or

(16) an amino acid residue at position 44 in the amino acid sequence shown in SEQ ID NO:1 or at a position corresponding to this position, is deleted or substituted with aspartic acid; and/or

(17) an amino acid residue at position 45 in the amino acid sequence shown in SEQ ID NO:1 or at a position corresponding to this position, is deleted or substituted with isoleucine; and/or

(18) an amino acid residue at position 46 in the amino acid sequence shown in SEQ ID NO:1 or at a position corresponding to this position, is deleted or substituted with valine; and/or

(19) an amino acid residue at position 49 in the amino acid sequence shown in SEQ ID NO:1 or at a position corresponding to this position, is deleted or substituted with aspartic acid, glycine or serine; and/or

(20) an amino acid residue at position 51 in the amino acid sequence shown in SEQ ID NO:1 or at a position corresponding to this position, is deleted or substituted with histidine; and/or

(21) an amino acid residue at position 52 in the amino acid sequence shown in SEQ ID NO:1 or at a position corresponding to this position, is deleted or substituted with phenylalanine, leucine or methionine; and/or

(22) an amino acid residue at position 54 in the amino acid sequence shown in SEQ ID NO:1 or at a position corresponding to this position, is deleted or substituted with arginine; and/or

(23) an amino acid residue at position 56 in the amino acid sequence shown in SEQ ID NO:1 or at a position corresponding to this position, is deleted or substituted with serine; and/or

(24) an amino acid residue at position 59 in the amino acid sequence shown in SEQ ID NO:1 or at a position corresponding to this position, is deleted or substituted with arginine; and/or

(25) an amino acid residue at position 60 in the amino acid sequence shown in SEQ ID NO:1 or at a position corresponding to this position, is deleted or substituted with histidine or tryptophan; and/or

(26) an amino acid residue at position 64 in the amino acid sequence shown in SEQ ID NO:1 or at a position corresponding to this position, is deleted or substituted with glutamic acid; and/or

(27) an amino acid residue at position 65 in the amino acid sequence shown in SEQ ID NO:1 or at a position corresponding to this position, is deleted or substituted with aspartic acid or glutamic acid; and/or

(28) an amino acid residue at position 67 in the amino acid sequence shown in SEQ ID NO:1 or at a position corresponding to this position, is deleted or substituted with cysteine or asparagine; and/or

(29) an amino acid residue at position 70 in the amino acid sequence shown in SEQ ID NO:1 or at a position corresponding to this position, is deleted or substituted with leucine or valine; and/or

(30) an amino acid residue at position 71 in the amino acid sequence shown in SEQ ID NO:1 or at a position corresponding to this position, is deleted or substituted with glycine or isoleucine; and/or

(31) an amino acid residue at position 73 in the amino acid sequence shown in SEQ ID NO:1 or at a position corresponding to this position, is deleted or substituted with proline; and/or

(32) an amino acid residue at position 74 in the amino acid sequence shown in SEQ ID NO:1 or at a position corresponding to this position, is deleted or substituted with proline; and/or

(33) an amino acid residue at position 75 in the amino acid sequence shown in SEQ ID NO:1 or at a position corresponding to this position, is deleted or substituted with glycine; and/or

(34) an amino acid residue at position 76 in the amino acid sequence shown in SEQ ID NO:1 or at a position corresponding to this position, is deleted or substituted with proline; and/or

(35) an amino acid residue at position 77 in the amino acid sequence shown in SEQ ID NO:1 or at a position corresponding to this position, is deleted or substituted with proline; and/or

(36) an amino acid residue at position 80 in the amino acid sequence shown in SEQ ID NO:1 or at a position corresponding to this position, is deleted or substituted with alanine or threonine; and/or

(37) an amino acid residue at position 81 in the amino acid sequence shown in SEQ ID NO:1 or at a position corresponding to this position, is deleted or substituted with glutamic acid, glycine, glutamine, arginine or threonine; and/or

(38) an amino acid residue at position 82 in the amino acid sequence shown in SEQ ID NO:1 or at a position corresponding to this position, is deleted or substituted with aspartic acid; and/or

(39) an amino acid residue at position 83 in the amino acid sequence shown in SEQ ID NO:1 or at a position corresponding to this position, is deleted or substituted with asparagine; and/or

(40) an amino acid residue at position 88 in the amino acid sequence shown in SEQ ID NO:1 or at a position corresponding to this position, is deleted or substituted with threonine; and/or

(41) an amino acid residue at position 89 in the amino acid sequence shown in SEQ ID NO:1 or at a position corresponding to this position, is deleted or substituted with glycine or serine; and/or

(42) an amino acid residue at position 90 in the amino acid sequence shown in SEQ ID NO:1 or at a position corresponding to this position, is deleted or substituted with proline or serine; and/or

(43) an amino acid residue at position 91 in the amino acid sequence shown in SEQ ID NO:1 or at a position corresponding to this position, is deleted or substituted with glycine, proline or serine; and/or

(44) an amino acid residue at position 92 in the amino acid sequence shown in SEQ ID NO:1 or at a position corresponding to this position, is deleted or substituted with threonine; and/or

(45) an amino acid residue at position 93 in the amino acid sequence shown in SEQ ID NO:1 or at a position corresponding to this position, is deleted or substituted with isoleucine; and/or

(46) an amino acid residue at position 94 in the amino acid sequence shown in SEQ ID NO:1 or at a position corresponding to this position, is deleted or substituted with alanine or serine; and/or

(47) an amino acid residue at position 98 in the amino acid sequence shown in SEQ ID NO:1 or at a position corresponding to this position, is deleted or substituted with threonine; and/or

(48) an amino acid residue at position 99 in the amino acid sequence shown in SEQ ID NO:1 or at a position corresponding to this position, is deleted or substituted with lysine; and/or

(49) an amino acid residue at position 115 in the amino acid sequence shown in SEQ ID NO:1 or at a position corresponding to this position, is deleted or substituted with valine; and/or

(50) an amino acid residue at position 118 in the amino acid sequence shown in SEQ ID NO:1 or at a position corresponding to this position, is deleted or substituted with threonine; and/or

(51) an amino acid residue at position 119 in the amino acid sequence shown in SEQ ID NO:1 or at a position corresponding to this position, is deleted or substituted with valine; and/or

(52) an amino acid residue at position 121 in the amino acid sequence shown in SEQ ID NO:1 or at a position corresponding to this position, is deleted or substituted with alanine; and/or

(53) an amino acid residue at position 123 in the amino acid sequence shown in SEQ ID NO:1 or at a position corresponding to this position, is deleted or substituted with arginine or asparagine; and/or

(54) an amino acid residue at position 127 in the amino acid sequence shown in SEQ ID NO:1 or at a position corresponding to this position, is deleted or substituted with asparagine; and/or

(55) an amino acid residue at position 133 in the amino acid sequence shown in SEQ ID NO:1 or at a position corresponding to this position, is deleted or substituted with serine; and/or

(56) an amino acid residue at position 135 in the amino acid sequence shown in SEQ ID NO:1 or at a position corresponding to this position, is deleted or substituted with cysteine; and/or

(57) an amino acid residue at position 136 in the amino acid sequence shown in SEQ ID NO:1 or at a position corresponding to this position, is deleted or substituted with glycine; and/or

(58) an amino acid residue at position 137 in the amino acid sequence shown in SEQ ID NO:1 or at a position corresponding to this position, is deleted or substituted with glutamic acid, proline or serine; and/or

(59) an amino acid residue at position 141 in the amino acid sequence shown in SEQ ID NO:1 or at a position corresponding to this position, is deleted or substituted with alanine or glycine; and/or

(60) an amino acid residue at position 147 in the amino acid sequence shown in SEQ ID NO:1 or at a position corresponding to this position, is deleted or substituted with leucine; and/or

(61) an amino acid residue at position 158 in the amino acid sequence shown in SEQ ID NO:1 or at a position corresponding to this position, is deleted or substituted with serine; and/or

(62) an amino acid residue at position 160 in the amino acid sequence shown in SEQ ID NO:1 or at a position corresponding to this position, is deleted or substituted with valine; and/or

(63) an amino acid residue at position 172 in the amino acid sequence shown in SEQ ID NO:1 or at a position corresponding to this position, is deleted or substituted with methionine; and/or

(64) an amino acid residue at position 174 in the amino acid sequence shown in SEQ ID NO:1 or at a position corresponding to this position, is deleted or substituted with phenylalanine; and/or

(65) an amino acid residue at position 175 in the amino acid sequence shown in SEQ ID NO:1 or at a position corresponding to this position, is deleted or substituted with threonine; and/or

(66) an amino acid residue at position 178 in the amino acid sequence shown in SEQ ID NO:1 or at a position corresponding to this position, is deleted or substituted with asparagine; and/or

(67) an amino acid residue at position 180 in the amino acid sequence shown in SEQ ID NO:1 or at a position corresponding to this position, is deleted or substituted with cysteine, glutamic acid, glycine, leucine, arginine or threonine; and/or

(68) an amino acid residue at position 183 in the amino acid sequence shown in SEQ ID NO:1 or at a position corresponding to this position, is deleted or substituted with aspartic acid; and/or

(69) an amino acid residue at position 184 in the amino acid sequence shown in SEQ ID NO:1 or at a position corresponding to this position, is deleted or substituted with proline; and/or

(70) an amino acid residue at position 186 in the amino acid sequence shown in SEQ ID NO:1 or at a position corresponding to this position, is deleted or substituted with methionine; and/or

(71) an amino acid residue at position 187 in the amino acid sequence shown in SEQ ID NO:1 or at a position corresponding to this position, is deleted or substituted with glutamic acid, glycine, methionine or valine; and/or

(72) an amino acid residue at position 189 in the amino acid sequence shown in SEQ ID NO:1 or at a position corresponding to this position, is deleted or substituted with glutamic acid or serine; and/or

(73) an amino acid residue at position 197 in the amino acid sequence shown in SEQ ID NO:1 or at a position corresponding to this position, is deleted or substituted with cysteine, lysine or leucine; and/or

(74) an amino acid residue at position 200 in the amino acid sequence shown in SEQ ID NO:1 or at a position corresponding to this position, is deleted or substituted with glutamic acid or threonine; and/or

(75) an amino acid residue at position 202 in the amino acid sequence shown in SEQ ID NO:1 or at a position corresponding to this position, is deleted or substituted with serine; and/or

(76) an amino acid residue at position 203 in the amino acid sequence shown in SEQ ID NO:1 or at a position corresponding to this position, is deleted or substituted with serine; and/or

(77) an amino acid residue at position 205 in the amino acid sequence shown in SEQ ID NO:1 or at a position corresponding to this position, is deleted or substituted with isoleucine or arginine; and/or

(78) an amino acid residue at position 206 in the amino acid sequence shown in SEQ ID NO:1 or at a position corresponding to this position, is deleted or substituted with arginine; and/or

(79) an amino acid residue at position 208 in the amino acid sequence shown in SEQ ID NO:1 or at a position corresponding to this position, is deleted or substituted with threonine; and/or

(80) an amino acid residue at position 211 in the amino acid sequence shown in SEQ ID NO:1 or at a position corresponding to this position, is deleted or substituted with lysine or arginine; and/or

(81) an amino acid residue at position 217 in the amino acid sequence shown in SEQ ID NO:1 or at a position corresponding to this position, is deleted or substituted with methionine; and/or

(82) an amino acid residue at position 240 in the amino acid sequence shown in SEQ ID NO:1 or at a position corresponding to this position, is deleted or substituted with glycine; and/or

(83) an amino acid residue at position 248 in the amino acid sequence shown in SEQ ID NO:1 or at a position corresponding to this position, is deleted or substituted with threonine; and/or

(84) an amino acid residue at position 252 in the amino acid sequence shown in SEQ ID NO:1 or at a position corresponding to this position, is deleted or substituted with lysine or serine; and/or

(85) an amino acid residue at position 256 in the amino acid sequence shown in SEQ ID NO:1 or at a position corresponding to this position, is deleted or substituted with arginine; and/or

(86) an amino acid residue at position 259 in the amino acid sequence shown in SEQ ID NO:1 or at a position corresponding to this position, is deleted or substituted with asparagine; and/or

(87) an amino acid residue at position 260 in the amino acid sequence shown in SEQ ID NO:1 or at a position corresponding to this position, is deleted or substituted with phenylalanine or histidine; and/or

(88) an amino acid residue at position 285 in the amino acid sequence shown in SEQ ID NO:1 or at a position corresponding to this position, is deleted or substituted with cysteine; and/or

(89) an amino acid residue at position 289 in the amino acid sequence shown in SEQ ID NO:1 or at a position corresponding to this position, is deleted or substituted with valine; and/or

(90) an amino acid residue at position 295 in the amino acid sequence shown in SEQ ID NO:1 or at a position corresponding to this position, is deleted or substituted with asparagine; and/or

(91) an amino acid residue at position 296 in the amino acid sequence shown in SEQ ID NO:1 or at a position corresponding to this position, is deleted or substituted with threonine; and/or

(92) an amino acid residue at position 302 in the amino acid sequence shown in SEQ ID NO:1 or at a position corresponding to this position, is deleted or substituted with arginine; and/or

(93) an amino acid residue at position 303 in the amino acid sequence shown in SEQ ID NO:1 or at a position corresponding to this position, is deleted or substituted with threonine; and/or

(94) an amino acid residue at position 307 in the amino acid sequence shown in SEQ ID NO:1 or at a position corresponding to this position, is deleted or substituted with histidine; and/or

(95) an amino acid residue at position 311 in the amino acid sequence shown in SEQ ID NO:1 or at a position corresponding to this position, is deleted or substituted with cysteine, proline or glutamine; and/or

(96) an amino acid residue at position 313 in the amino acid sequence shown in SEQ ID NO:1 or at a position corresponding to this position, is deleted or substituted with leucine, arginine, serine, threonine, valine or tyrosine; and/or

(97) an amino acid residue at position 315 in the amino acid sequence shown in SEQ ID NO:1 or at a position corresponding to this position, is deleted or substituted with histidine, lysine or threonine; and/or

(98) an amino acid residue at position 316 in the amino acid sequence shown in SEQ ID NO:1 or at a position corresponding to this position, is deleted or substituted with histidine; and/or

(99) an amino acid residue at position 318 in the amino acid sequence shown in SEQ ID NO:1 or at a position corresponding to this position, is deleted or substituted with aspartic acid.

The invention also relates to variants as defined in (1) to (99) hereinabove, wherein the amino acid residue indicated as substituting the amino acid residue at the position in SEQ ID NO: 1 is not that particular amino acid residue but an amino acid residue which is conservative in relation to the indicated substituting amino acid.

Whether an amino acid is conservative with respect to another amino acid can be judged according to means and methods known in the art and as described herein above. One possibility is the PAM 250 matrix; alternatively, the Blosum Family Matrices can be used.

In a preferred embodiment, the HIV kinase variant according to the invention showing an improved activity in converting 3-hydroxyisovalerate (HIV) into 3-phosphonoxyisovalerate (PIV) is characterized in that contains at least one deletion, substitution and/or insertion wherein the deletion/insertion/substitution is at position 252 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 240, 248, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: E252S.

In a preferred embodiment, the HIV kinase variant according to the invention showing an improved activity in converting 3-hydroxyisovalerate (HIV) into 3-phosphonoxyisovalerate (PIV) is characterized in that contains at least one deletion, substitution and/or insertion wherein the deletion/insertion/substitution is at position 59 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: H59R.

In a preferred embodiment, the HIV kinase variant according to the invention showing an improved activity in converting 3-hydroxyisovalerate (HIV) into 3-phosphonoxyisovalerate (PIV) is characterized in that contains at least one deletion, substitution and/or insertion wherein the deletion/insertion/substitution is at position 6 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: I6L.

In a preferred embodiment, the HIV kinase variant according to the invention showing an improved activity in converting 3-hydroxyisovalerate (HIV) into 3-phosphonoxyisovalerate (PIV) is characterized in that contains at least one deletion, substitution and/or insertion wherein the deletion/insertion/substitution is at position 200 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E or L200T.

In a preferred embodiment, the HIV kinase variant according to the invention showing an improved activity in converting 3-hydroxyisovalerate (HIV) into 3-phosphonoxyisovalerate (PIV) is characterized in that contains at least one deletion, substitution and/or insertion wherein the deletion/insertion/substitution is at position 240 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: S240G.

In a preferred embodiment, the HIV kinase variant according to the invention showing an improved activity in converting 3-hydroxyisovalerate (HIV) into 3-phosphonoxyisovalerate (PIV) is characterized in that contains at least one deletion, substitution and/or insertion wherein the deletion/insertion/substitution is at position 26 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: V26F.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 6 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-I6L.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 240 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-S240G.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 137 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-A137S.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 285 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-E285C.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 89 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-F89G.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 90 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-G90P.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 211 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-H211K or L200E-H211R.

In a preferred embodiment, the variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 135 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-L135C.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 25 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-P25R.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 197 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-R197K or L200E-R197L.

In a preferred embodiment, the HIV kinase variant according to the invention showing an improved activity in converting 3-hydroxyisovalerate (HIV) into 3-phosphonoxyisovalerate PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 307 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-R307H.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 315 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 316 and 318 in the amino acid sequence shown in SEQ ID NO:1.

Preferably, such a variant has the following substitution in the amino acid sequence shown in SEQ ID NO:1 or at positions corresponding to this position: L200E-R315K.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 76 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-R76P.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 82 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-S82D.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 77 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V77P.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 313 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 315, 316 and 318 in the amino acid sequence shown in SEQ ID NO:1.

Preferably, such a variant has the following substitution in the amino acid sequence shown in SEQ ID NO:1 or at positions corresponding to this position: L200E-W313R, L200E-W313T or L200E-W313Y.

In a preferred embodiment, the HIV kinase variant according to the invention showing an improved activity in converting 3-hydroxyisovalerate (HIV) into 3-phosphonoxyisovalerate (PIV) is characterized in that contains at least two deletions, substitutions and/or insertions wherein the deletion/insertion/substitution is at position 200 in the amino acid sequence shown in SEQ ID NO:1 or at a position corresponding to this position and another deletion/insertion/substitution is at position 81 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-Y81E or L200E-Y81T.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 49 in the amino acid sequence shown in SEQ ID NO:1 or at a position corresponding to this position and another deletion/insertion/substitution is at position 74 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-E49S-V74P.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 67 in the amino acid sequence shown in SEQ ID NO:1 or at a position corresponding to this position and another deletion/insertion/substitution is at position 197 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-S67N-R197K.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 73 in the amino acid sequence shown in SEQ ID NO:1 or at a position corresponding to this position and another deletion/insertion/substitution is at position 74 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-S73P-V74P.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 137 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-A137P.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 285 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-E285C.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 89 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-F89S.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 211 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-H211K or L200E-V74P-H211R.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 135 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-L135C.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 136 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-R136G.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 197 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-R197L.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 315 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-R315H or L200E-V74P-R315K.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 91 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-T91G, L200E-V74P-T91P or L200E-V74P-T91S.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 74 in the amino acid sequence shown in SEQ ID NO:1 or at a position corresponding to this position and another deletion/insertion/substitution is at position 313 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V74P-W313T.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 77 in the amino acid sequence shown in SEQ ID NO:1 or at a position corresponding to this position and another deletion/insertion/substitution is at position 211 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 33, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V77P-H211R.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 77 in the amino acid sequence shown in SEQ ID NO:1 or at a position corresponding to this position and another deletion/insertion/substitution is at position 197 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V77P-R197L.

In a preferred embodiment, the HIV kinase variant according to the invention showing an improved activity in converting 3-hydroxyisovalerate (HIV) into 3-phosphonoxyisovalerate (PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 77 in the amino acid sequence shown in SEQ ID NO:1 or at a position corresponding to this position and another deletion/insertion/substitution is at position 315 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 316 and 318 in the amino acid sequence shown in SEQ ID NO:1.

Preferably, such a variant has the following substitution in the amino acid sequence shown in SEQ ID NO:1 or at positions corresponding to this position: L200E-V77P-R315H or L200E-V77P-R315K.

In a preferred embodiment, the HIV kinase variant according to the invention showing an improved activity in converting 3-hydroxyisovalerate (HIV) into 3-phosphonoxyisovalerate a(PIV) is characterized in that contains at least three deletions, substitutions and/or insertions wherein the deletion/insertion/substitution is at position 200 in the amino acid sequence shown in SEQ ID NO:1 or at a position corresponding to this position and another deletion/insertion/substitution is at position 77 in the amino acid sequence shown in SEQ ID NO:1 or at a position corresponding to this position and another deletion/insertion/substitution is at position 313 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 315, 316 and 318 in the amino acid sequence shown in SEQ ID NO:1.

Preferably, such a variant has the following substitution in the amino acid sequence shown in SEQ ID NO:1 or at positions corresponding to this position: L200E-V77P-W313R, L200E-V77P-W313T or L200E-V77P-W313Y.

In even more preferred embodiments, the HIV kinase variant according to the invention showing an improved activity in converting 3-hydroxyisovalerate (HIV) into 3-phosphonoxyisovalerate (PIV) is characterized in that it has multiple mutations. As it is exemplified in the examples further below, variants have been found bearing multiple mutations which exhibit an increase in the reaction rate of the conversion of 3-hydroxyisovalerate (HIV) into 3-phosphonoxyisovalerate (PIV). These variants bearing multiple mutations are summarized in the following:

Accordingly, in a very preferred embodiment, the HIV kinase variant according to the invention is characterized in that it comprises deletions, substitutions and/or insertions wherein the deletions/insertions/substitutions are at positions 200, 49, 77 and 315 in the amino acid sequence shown in SEQ ID NO:1 or at positions corresponding to these positions. Preferably, such a variant has the following substitutions in the amino acid sequence shown in SEQ ID NO:1 or at positions corresponding to these position: L200E-E49D-V77P-R315K.

In another very preferred embodiment, the HIV kinase variant according to the invention is characterized in that it comprises deletions, substitutions and/or insertions wherein the deletions/insertions/substitutions are at positions 200, 74, 90 and 91 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-G90P-T91S, L200E-V74P-G90S-T91G, L200E-V74P-G90S-T91P or L200E-V74P-G90S-T91S.

In another very preferred embodiment, the HIV kinase variant according to the invention is characterized in that it comprises deletions, substitutions and/or insertions wherein the deletions/insertions/substitutions are at positions 200, 76, 135, 197 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-R76P-L135C-R197L-H211R.

In another very preferred embodiment, the HIV kinase variant according to the invention is characterized in that it comprises deletions, substitutions and/or insertions wherein the deletions/insertions/substitutions are at positions 200, 76, 81, 135, 197 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-R76P-Y81T-L135C-R197L-H211R.

In another very preferred embodiment, the HIV kinase variant according to the invention is characterized in that it comprises deletions, substitutions and/or insertions wherein the deletions/insertions/substitutions are at positions 200, 76, 81, 1997 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-R76P-Y81T-R197L-H211R.

In another very preferred embodiment, the HIV kinase variant according to the invention is characterized in that it comprises deletions, substitutions and/or insertions wherein the deletions/insertions/substitutions are at positions 200, 74, 77 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-H211K or L200E-V74P-V77P-H211R.

In another very preferred embodiment, the HIV kinase variant according to the invention is characterized in that it comprises deletions, substitutions and/or insertions wherein the deletions/insertions/substitutions are at positions 200, 74, 77, 135, 197 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-L135C-R197L-H211R.

In another very preferred embodiment, the HIV kinase variant according to the invention is characterized in that it comprises deletions, substitutions and/or insertions wherein the deletions/insertions/substitutions are at positions 200, 74, 77, 197 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R197L-H211R.

In another very preferred embodiment, the HIV kinase variant according to the invention is characterized in that it comprises deletions, substitutions and/or insertions wherein the deletions/insertions/substitutions are at positions 200, 77, 211 and 313 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-H211K-W313T.

In another very preferred embodiment, the HIV kinase variant according to the invention is characterized in that it comprises deletions, substitutions and/or insertions wherein the deletions/insertions/substitutions are at positions 200, 77, 135 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211K or L200E-V77P-L135C-H211R.

In another very preferred embodiment, the HIV kinase variant according to the invention is characterized in that it comprises deletions, substitutions and/or insertions wherein the deletions/insertions/substitutions are at positions 200, 77, 197 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-R197C-H211R.

In another very preferred embodiment, the HIV kinase variant according to the invention is characterized in that it comprises deletions, substitutions and/or insertions wherein the deletions/insertions/substitutions are at positions 200, 77, 94, 135, 197 and 211 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-V94S-L135C-R197L-H211R.

In another very preferred embodiment, the HIV kinase variant according to the invention is characterized in that it comprises deletions, substitutions and/or insertions wherein the deletions/insertions/substitutions are at positions 200, 135, 211, 76, 81 and 197 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-L135C-H211R-R76P-Y81T-R197L.

In another very preferred embodiment, the HIV kinase variant according to the invention is characterized in that it comprises deletions, substitutions and/or insertions wherein the deletions/insertions/substitutions are at positions 200, 77, 135, 211, 197, 80 and 81 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-R197L-R80A-Y81R.

In another very preferred embodiment, the HIV kinase variant according to the invention is characterized in that it comprises deletions, substitutions and/or insertions wherein the deletions/insertions/substitutions are at positions 200, 77, 135, 211, 80 and 81 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-R80A-Y81Q or L200E-V77P-L135C-H211R-R80A-Y81R or L200E-V77P-L135C-H211R-R80T-Y81R.

In another very preferred embodiment, the HIV kinase variant according to the invention is characterized in that it comprises deletions, substitutions and/or insertions wherein the deletions/insertions/substitutions are at positions 200, 77, 135, 211 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-S141A or L200E-V77P-L135C-H211R-S141G.

In another very preferred embodiment, the HIV kinase variant according to the invention is characterized in that it comprises deletions, substitutions and/or insertions wherein the deletions/insertions/substitutions are at positions 200, 77, 135, 211 and 65 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-T65D or L200E-V77P-L135C-H211R-T65E.

In another very preferred embodiment, the HIV kinase variant according to the invention is characterized in that it comprises deletions, substitutions and/or insertions wherein the deletions/insertions/substitutions are at positions 200, 77, 135, 211, 74 and 197 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R197L.

In another very preferred embodiment, the HIV kinase variant according to the invention is characterized in that it comprises deletions, substitutions and/or insertions wherein the deletions/insertions/substitutions are at positions 200, 135, 211, 74, 197, 80 and 81 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R197L-R80A-Y81R or L200E-V77P-L135C-H211R-V74P-R197L-R80T-Y81R.

In another very preferred embodiment, the HIV kinase variant according to the invention is characterized in that it comprises deletions, substitutions and/or insertions wherein the deletions/insertions/substitutions are at positions 200, 77, 135, 211, 74, 80 and 81 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80T-Y81R.

In another very preferred embodiment, the HIV kinase variant according to the invention is characterized in that it comprises deletions, substitutions and/or insertions wherein the deletions/insertions/substitutions are at positions 200, 77, 135, 211 and 183 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-Y183D.

In another very preferred embodiment, the HIV kinase variant according to the invention is characterized in that it comprises deletions, substitutions and/or insertions wherein the deletions/insertions/substitutions are at positions 200, 77, 135, 211 and 3 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-Y3H.

In another very preferred embodiment, the HIV kinase variant according to the invention is characterized in that it comprises deletions, substitutions and/or insertions wherein the deletions/insertions/substitutions are at positions 200, 74, 197, 211, 49 and 91 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-E49G-T91S.

In another very preferred embodiment, the HIV kinase variant according to the invention is characterized in that it comprises deletions, substitutions and/or insertions wherein the deletions/insertions/substitutions are at positions 200, 74, 197, 211, 90, 91, 135 and 137 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G90P-T91S-L135C-A137P.

In another very preferred embodiment, the HIV kinase variant according to the invention is characterized in that it comprises deletions, substitutions and/or insertions wherein the deletions/insertions/substitutions are at positions 200, 74, 197, 211, 32, 73, 81, 90, 91, 135 and 136 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-H32D-S73P-Y81R-G90S-T91S-L135C-R136G.

In another very preferred embodiment, the HIV kinase variant according to the invention is characterized in that it comprises deletions, substitutions and/or insertions wherein the deletions/insertions/substitutions are at positions 200, 74, 197, 211 and 135 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-L135C.

In another very preferred embodiment, the HIV kinase variant according to the invention is characterized in that it comprises deletions, substitutions and/or insertions wherein the deletions/insertions/substitutions are at positions 200, 74, 197, 211, 80, 90, 91 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-G90S-T91G-R307H.

In another very preferred embodiment, the HIV kinase variant according to the invention is characterized in that it comprises deletions, substitutions and/or insertions wherein the deletions/insertions/substitutions are at positions 200, 74, 197, 211, 80, 135 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-L135C-R307H.

In another very preferred embodiment, the HIV kinase variant according to the invention is characterized in that it comprises deletions, substitutions and/or insertions wherein the deletions/insertions/substitutions are at positions 200, 74, 197, 211, 80, 91 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-T91G-R307H.

In another very preferred embodiment, the HIV kinase variant according to the invention is characterized in that it comprises deletions, substitutions and/or insertions wherein the deletions/insertions/substitutions are at positions 200, 74, 197, 211, 80, 81 and 91 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-Y81R-T91G.

In another very preferred embodiment, the HIV kinase variant according to the invention is characterized in that it comprises deletions, substitutions and/or insertions wherein the deletions/insertions/substitutions are at positions 200, 74, 197, 211, 73, 81 and 135 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-S73P-Y81R-L135C.

In another very preferred embodiment, the HIV kinase variant according to the invention is characterized in that it comprises deletions, substitutions and/or insertions wherein the deletions/insertions/substitutions are at positions 200, 74, 197, 211, 81 and 137 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-A137S.

In another very preferred embodiment, the HIV kinase variant according to the invention is characterized in that it comprises deletions, substitutions and/or insertions wherein the deletions/insertions/substitutions are at positions 200, 74, 197, 211, 81, 90, 91 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-G90S-T91S-R307H.

In another very preferred embodiment, the HIV kinase variant according to the invention is characterized in that it comprises deletions, substitutions and/or insertions wherein the deletions/insertions/substitutions are at positions 200, 74, 197, 211, 81, 90, 91, 93, 135 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-G90S-T91S-T93I-L135C-R307H.

In another very preferred embodiment, the HIV kinase variant according to the invention is characterized in that it comprises deletions, substitutions and/or insertions wherein the deletions/insertions/substitutions are at positions 200, 74, 197, 211, 81, 135 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-L135C-R307H.

In another very preferred embodiment, the HIV kinase variant according to the invention is characterized in that it comprises deletions, substitutions and/or insertions wherein the deletions/insertions/substitutions are at positions 200, 74, 197, 211, 81, 91, 137 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-T91G-A137S-R307H.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 137 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-A137E.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 208 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-A208T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 23, 94 and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-A23T-V94A-K123N.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 43 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-C43S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 70, 88 and 92 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-D70V-A88T-K92T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 158 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-F158S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 121 and 259 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-G121A-S259N.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 44 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-G44D.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 44 and 205 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-G44D-K205I.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 7, 45, 49, 67, 160 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-G7V-S45I-E49D-S67C-A160V-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 46 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-I46V.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 256 and 302 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-K256R-K302R.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 133 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-N133S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 24 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-N24D.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 24, 141, 184 and 208 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-N24D-S141A-Q184P-A208T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 25, 71, 147 and 302 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-P25L-N71I-F147L-K302R.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 184 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-Q184P.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 99 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-Q99K.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141A.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 184 and 208 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-Q184P-A208T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 83 and 295 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S83N-I295N.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 8 and 115 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S8T-I1115V.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 65 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-T65E.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 65, 141, 184 and 208 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-T65E-S141A-Q184P-A208T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 260 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-Y260H.

In another very preferred embodiment, the HIV kinase variant according to the invention is characterized in that it comprises deletions, substitutions and/or insertions wherein the deletions/insertions/substitutions are at positions 200, 74, 197, 211, 43, 44, 80, 81, 133, 141, 260 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-G44D-R80A-Y81R-N133S-S141G-Y260H-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 135 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-L135C-S141G.

In another very preferred embodiment, the HIV kinase variant according to the invention is characterized in that it comprises deletions, substitutions and/or insertions wherein the deletions/insertions/substitutions are at positions 200, 74, 197, 211, 43, 99, 133, 135, 136, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Q99K-N133S-L135C-R136G-S141A-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 99, 133, 135, 136, 141, 303 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Q99K-N133S-L135C-R136G-S141G-K303T-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 99, 133, 135, 136, 141, 260, 303 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Q99K-N133S-L135C-R136G-S141G-Y260H-K303T-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 99, 133, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Q99K-N133S-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 99, 135, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Q99K-L135C-S141G-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 99, 133, 135, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Q99K-N133S-L135C-S141G-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 99, 133, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Q99K-N133S-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 91, 99, 135, 136, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-T91S-Q99K-L135C-R136G-S141G-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 81, 133, 141, 303 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Y81R-N133S-S141G-K303T-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 81, 99, 133, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Y81R-Q99K-N133S-S141G-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 81, 91, 99, 135, 136, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Y81R-T91S-Q99K-L135C-R136G-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 81, 91, 99, 135, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Y81R-T91S-Q99K-L135C-S141A-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 80, 81, 91, 99, 133, 135, 136, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-R80A-Y81R-T91S-Q99K-N133S-L135C-R136G-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-S141G-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 91, 133, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-T91S-N133S-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 135, 136, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-L135C-R136G-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 99, 133, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-Q99K-N133S-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 141, 252, 260 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-S141G-E252K-Y260H-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 91, 135, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-T91S-L135C-S141A-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 91, 133, 136, 141, 303 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-T91S-N133S-R136G-S141G-K303T-R307H.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 91, 133, 141, 260, 303 and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-T91S-N133S-S141G-Y260H-K303T-G311C.

In another very preferred embodiment, the HIV kinase variant according to the invention is characterized in that it comprises deletions, substitutions and/or insertions wherein the deletions/insertions/substitutions are at positions 200, 74, 197, 211, 43, 81, 91, 99, 135, 136, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-C43S-Y81R-T91S-Q99K-L135C-R136G-S141G-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 99, 141, 260 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Q99K-S141G-Y260H-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 80, 133, 135, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-R80A-N133S-L135C-S141G-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 80, 99, 135, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-R80A-Q99K-L135C-S141G-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 80, 141, 260 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-R80A-S141G-Y260H-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 80, 91, 99, 133, 135, 141, 260 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-R80A-T91S-Q99K-N133S-L135C-S141G-Y260H-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 80, 81, 133, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-R80A-Y81R-N133S-S141G-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 80, 81, 91, 133, 135, 141, 180, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-R80A-Y81R-T91S-N133S-L135C-S141A-A180T-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 73, 81, 91, 99, 135, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-S73P-Y81R-T91S-Q99K-L135C-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 91, 123, 135, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-T91S-K123R-L135C-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 91, 133, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-T91S-N133S-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 91, 99, 118, 133, 135, 141, 175, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-T91S-Q99K-A118T-N133S-L135C-S141G-S175T-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 91, 99, 135, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-T91S-Q99K-L135C-S141G-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 91, 99, 135, 141, 260, 303 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-T91S-Q99K-L135C-S141G-Y260H-K303T-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 91, 99, 135, 141, 260 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-T91S-Q99K-L135C-S141G-Y260H-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 91, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-T91S-S141G-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 99, 135, 141, 260, 303 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-Q99K-L135C-S141G-Y260H-K303T-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 99, 133, 136, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-Q99K-N133S-R136G-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-S141G-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 141 and 260 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-S141G-Y260H.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 141, 260 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-S141G-Y260H-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 91, 135, 141, 303 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-T91S-L135C-S141G-K303T-R307H.

In another very preferred embodiment, the HIV kinase variant according to the invention is characterized in that it comprises deletions, substitutions and/or insertions wherein the deletions/insertions/substitutions are at positions 200, 74, 197, 211, 44, 197, 211, 44, 81, 91, 135, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-T91S-L135C-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 91, 99, 133, 141 and 260 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-T91S-Q99K-N133S-S141G-Y260H.

In another very preferred embodiment, the HIV kinase variant according to the invention is characterized in that it comprises deletions, substitutions and/or insertions wherein the deletions/insertions/substitutions are at positions 200, 74, 197, 211, 44, 81, 91, 99, 141, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G44D-Y81R-T91S-Q99K-S141G-Y260H-K303T.

In another very preferred embodiment, the HIV kinase variant according to the invention is characterized in that it comprises deletions, substitutions and/or insertions wherein the deletions/insertions/substitutions are at positions 200, 74, 197, 211, 90, 91, 135 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G90P-T91S-L135C-S141A.

In another very preferred embodiment, the HIV kinase variant according to the invention is characterized in that it comprises deletions, substitutions and/or insertions wherein the deletions/insertions/substitutions are at positions 200, 74, 197, 211, 90, 91, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-G90S-T91S-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 135, 137 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-L135C-A137S-R307H.

In another very preferred embodiment, the HIV kinase variant according to the invention is characterized in that it comprises deletions, substitutions and/or insertions wherein the deletions/insertions/substitutions are at positions 200, 74, 197, 211, 135, 137, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-L135C-A137S-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 135, 136 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-L135C-R136G-S141A.

In another very preferred embodiment, the HIV kinase variant according to the invention is characterized in that it comprises deletions, substitutions and/or insertions wherein the deletions/insertions/substitutions are at positions 200, 74, 197, 211, 135 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-L135C-S141A.

In another very preferred embodiment, the HIV kinase variant according to the invention is characterized in that it comprises deletions, substitutions and/or insertions wherein the deletions/insertions/substitutions are at positions 200, 74, 197, 211, 135, 141 and 289 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-L135C-S141A-A289V.

In another very preferred embodiment, the HIV kinase variant according to the invention is characterized in that it comprises deletions, substitutions and/or insertions wherein the deletions/insertions/substitutions are at positions 200, 74, 197, 211, 135, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-L135C-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 80, 127, 135 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-D127N-L135C-S141A.

In another very preferred embodiment, the HIV kinase variant according to the invention is characterized in that it comprises deletions, substitutions and/or insertions wherein the deletions/insertions/substitutions are at positions 200, 74, 197, 211, 80, 90, 91, 135 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-G90S-T91G-L135C-S141A.

In another very preferred embodiment, the HIV kinase variant according to the invention is characterized in that it comprises deletions, substitutions and/or insertions wherein the deletions/insertions/substitutions are at positions 200, 74, 197, 211, 80, 90, 91, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-G90S-T91S-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 80, 135, 136 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-L135C-R136G-S141A.

In another very preferred embodiment, the HIV kinase variant according to the invention is characterized in that it comprises deletions, substitutions and/or insertions wherein the deletions/insertions/substitutions are at positions 200, 74, 197, 211, 80, 91, 137, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-T91G-A137S-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 80, 81, 137, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-Y81R-A137P-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 80, 81, 135 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-Y81R-L135C-S141A.

In another very preferred embodiment, the HIV kinase variant according to the invention is characterized in that it comprises deletions, substitutions and/or insertions wherein the deletions/insertions/substitutions are at positions 200, 74, 197, 211, 80, 81, 135, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-R80A-Y81R-L135C-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-S141A.

In another very preferred embodiment, the HIV kinase variant according to the invention is characterized in that it comprises deletions, substitutions and/or insertions wherein the deletions/insertions/substitutions are at positions 200, 74, 197, 211, 73, 80, 135 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-S73P-R80A-L135C-R307H.

In another very preferred embodiment, the HIV kinase variant according to the invention is characterized in that it comprises deletions, substitutions and/or insertions wherein the deletions/insertions/substitutions are at positions 200, 74, 197, 211, 73, 80, 91, 135, 137, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-S73P-R80A-T91S-L135C-A137S-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 73, 80, 81, 135, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-S73P-R80A-Y81R-L135C-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 73, 91, 135, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-S73P-T91G-L135C-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 73, 91, 135, 137, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-S73P-T91S-L135C-A137P-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 91, 135, 136 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-T91G-L135C-R136G-S141A.

In another very preferred embodiment, the HIV kinase variant according to the invention is characterized in that it comprises deletions, substitutions and/or insertions wherein the deletions/insertions/substitutions are at positions 200, 74, 197, 211, 91, 135, 137 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-T91P-L135C-A137S-S141A.

In another very preferred embodiment, the HIV kinase variant according to the invention is characterized in that it comprises deletions, substitutions and/or insertions wherein the deletions/insertions/substitutions are at positions 200, 74, 197, 211, 91, 135, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-T91P-L135C-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 91, 137 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-T91S-A137P-S141A.

In another very preferred embodiment, the HIV kinase variant according to the invention is characterized in that it comprises deletions, substitutions and/or insertions wherein the deletions/insertions/substitutions are at positions 200, 74, 197, 211, 81, 137 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-A137P-S141A.

In another very preferred embodiment, the HIV kinase variant according to the invention is characterized in that it comprises deletions, substitutions and/or insertions wherein the deletions/insertions/substitutions are at positions 200, 74, 197, 211, 81 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-S141A.

In another very preferred embodiment, the HIV kinase variant according to the invention is characterized in that it comprises deletions, substitutions and/or insertions wherein the deletions/insertions/substitutions are at positions 200, 74, 197, 211, 81, 141 and 307 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-S141A-R307H.

In another very preferred embodiment, the HIV kinase variant according to the invention is characterized in that it comprises deletions, substitutions and/or insertions wherein the deletions/insertions/substitutions are at positions 200, 74, 197, 211, 81, 91, 135 and 137 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-T91G-L135C-A137S.

In another very preferred embodiment, the HIV kinase variant according to the invention is characterized in that it comprises deletions, substitutions and/or insertions wherein the deletions/insertions/substitutions are at positions 200, 74, 197, 211, 81, 91 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-T91G-S141A.

In another very preferred embodiment, the HIV kinase variant according to the invention is characterized in that it comprises deletions, substitutions and/or insertions wherein the deletions/insertions/substitutions are at positions 200, 74, 197, 211, 81, 91 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-R197L-H211R-Y81R-T91S-S141A.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81G-R197L-S141G.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 43, 99, 133 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141A-C43S-Q99K-N133S-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 43, 99, 133, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141A-C43S-Q99K-N133S-Y260H-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 44, 133 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141A-G44D-N133S-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141A-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 178 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-A178N.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 180 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-A180C, L200E-V77P-L135C-H211R-V74P-R80A-Y81R-R197L-S141G-A180E, L200E-V77P-L135C-H211R-V74P-R80A-Y81R-R197L-S141G-A180G, L200E-V77P-L135C-H211R-V74P-R80A-Y81R-R197L-S141G-A180L, or L200E-V77P-L135C-H211R-V74P-R80A-Y81R-R197L-S141G-A180R.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 54 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-A54R.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 43 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-C43G.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 43, 44, 133 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-C43S-G44D-N133S-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 43, 133 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-C43S-N133S-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 43, 133, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-C43S-N133S-Y260H-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 43, 99, 133 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-C43S-Q99K-N133S-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 43, 99, 133, 260, 303 and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-C43S-Q99K-N133S-Y260H-K303T-S141G.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 189 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-D189E or L200E-V77P-L135C-H211R-V74P-R80A-Y81R-R197L-S141G-D189S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 70 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-D70L.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 217 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-E217M.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 296 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-E296T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 56 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-E56S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-G311P.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-G311Q.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 44, 133 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-G44D-N133S-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 64 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-G64E.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 7 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-G7L or L200E-V77P-L135C-H211R-V74P-R80A-Y81R-R197L-S141G-G7Q.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 119 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-I119V.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 52 and 202 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-I52F-P202S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 52 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-I52L or L200E-V77P-L135C-H211R-V74P-R80A-Y81R-R197L-S141G-I52M.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 60 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-I60H or L200E-V77P-L135C-H211R-V74P-R80A-Y81R-R197L-S141G-I60W.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 133 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-N133S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 133 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-N133S-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 133, 260 and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-N133S-Y260H-K303T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 248 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-N248T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 71 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-N71G.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 187 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-P187E, L200E-V77P-L135C-H211R-V74P-R80A-Y81R-R197L-S141G-P187G, L200E-V77P-L135C-H211R-V74P-R80A-Y81R-R197L-S141G-P187M or L200E-V77P-L135C-H211R-V74P-R80A-Y81R-R197L-S141G-P187V.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 315 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-R315T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 75 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-R75G.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 172 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-S172M.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 5 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-S5A or L200E-V77P-L135C-H211R-V74P-R80A-Y81R-R197L-S141G-S5F.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 8 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-S8C.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 98 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-S98T.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 9 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-T9H.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 171 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-V17I.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141, 17 and 25 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-V17L-P25S.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 313 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-W313L, L200E-V77P-L135C-H211R-V74P-R80A-Y81R-R197L-S141G-W313S or L200E-V77P-L135C-H211R-V74P-R80A-Y81R-R197L-S141G-W313V.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 174 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-Y174F.

In another very preferred embodiment, the HIV kinase variant according to the invention is characterized in that it comprises deletions, substitutions and/or insertions wherein the deletions/insertions/substitutions are at positions 200, 77, 135, 211, 74, 80, 81, 197, 141 and 260 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V77P-L135C-H211R-V74P-R80A-Y81R-R197L-S141G-Y260F.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 7, 52, 172, and 313 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-G7L-I52L-S172M-W313V.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 17, 25, 70, 98, and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-V17L-P25S-D70L-S98T-G311P.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 7, 17, and 60 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-G7Q-V17L-I60H.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 7, and 52 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-G7Q-I52L.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 7, 52, and 313 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-G7Q-I52L-W313L.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 70, 98, and 315 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-D70L-S98T-R315H.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 70, 98, and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-D70L-S98T-G311P.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 7, 52, 172, and 313 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-G7Q-I52L-S172M-W313L.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 52, 98, 174, and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-I52L-S98T-Y174F-G311P.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 25, 60, and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-P25S-I60H-G311P.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 5, 7, 17, 25, 70, and 174 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-S5A-G7Q-V17L-P25S-D70L-Y174F.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 17, 25, 70, and 98 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-V17L-P25S-D70L-S98T.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 25, 98, and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-P25S-S98T-G311P.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, and 60 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-I60H.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 25, 52, 98, and 174 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-P25S-I52L-S98T-Y174F.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 7, 25, and 52 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-G7Q-P25S-I52L.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 25, 52, 98, and 311 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-P25S-I52L-S98T-G311P.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 25, 119, and 313 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-P25S-I119V-W313S.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 25, and 98 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-P25S-S98T.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 7, 25, and 60 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-G7Q-P25S-I60H.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 25, and 60 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-P25S-I60H.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 52, and 98 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-I52L-S98T.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 98, 119, and 174 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-S98T-I119V-Y174F.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 17, and 51 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-V17L-R51 H.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, 98, 311, and 313 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-S98T-G311P-W313S.

In another very preferred embodiment, the HIV kinase variant according to the invention is characterized in that it comprises deletions, substitutions and/or insertions wherein the deletions/insertions/substitutions are at positions 200, 74, 77, 80, 81, 135, 141, 197, 211, and 52 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-V74P-V77P-R80A-Y81R-L135C-S141G-R197L-H211R-I52L.

In another very preferred embodiment, the HIV kinase variant according to the invention is characterized in that it comprises deletions, substitutions and/or insertions wherein the deletions/insertions/substitutions are at positions 200, 43, 74, 80, 81, 133, 141, 197, 211, 303, 307, 7, and 52 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-C43S-V74P-R80A-Y81R-N133S-S141G-R197L-H211R-K303T-R307H-G7Q-I52L.

In another very preferred embodiment, the HIV kinase variant according to the invention is characterized in that it comprises deletions, substitutions and/or insertions wherein the deletions/insertions/substitutions are at positions 200, 43, 74, 80, 81, 133, 141, 197, 211, 303, 307, 7, 52, 172, 313, and 186 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-C43S-V74P-R80A-Y81R-N133S-S141G-R197L-H211R-K303T-R307H-G7L-I52L-S172M-W313V-N186M.

In another very preferred embodiment, the HIV kinase variant according to the invention is characterized in that it comprises deletions, substitutions and/or insertions wherein the deletions/insertions/substitutions are at positions 200, 43, 74, 80, 81, 133, 141, 197, 211, 303, 307, 203, 205, and 206 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-C43S-V74P-R80A-Y81R-N133S-S141G-R197L-H211R-K303T-R307H-A203S-K205R-K206R.

In another very preferred embodiment, the HIV kinase variant according to the invention is characterized in that it comprises deletions, substitutions and/or insertions wherein the deletions/insertions/substitutions are at positions 200, 43, 74, 80, 81, 133, 141, 197, 211, 303, 307, 14, 16, and 17 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-C43S-V74P-R80A-Y81R-N133S-S141G-R197L-H211R-K303T-R307H-I14V-V16I-V17I.

In another very preferred embodiment, the HIV kinase variant according to the invention is characterized in that it comprises deletions, substitutions and/or insertions wherein the deletions/insertions/substitutions are at positions 200, 43, 74, 80, 81, 133, 141, 197, 211, 303, 307, 315, 316, and 318 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L200E-C43S-V74P-R80A-Y81R-N133S-S141G-R197L-H211R-K303T-R307H-R315H-R316H-E318D.

The present invention also provides a HIV kinase variant showing an improved activity in converting 3-hydroxyisovalerate (HIV) into 3-phosphonoxyisovalerate (PIV), wherein the HIV kinase variant has a modification at position 200 in the amino acid sequence shown in SEQ ID NO:1 or at a position corresponding to this position and wherein said variant further has one or more substitutions, deletions and/or insertions in comparison to the corresponding sequence from which it is derived.

Thus, the present invention provides a HIV kinase variant showing an improved activity in converting 3-hydroxyisovalerate (HIV) into 3-phosphonoxyisovalerate (PIV), wherein the HIV kinase variant is characterized in that it contains at least one deletion, substitution and/or insertion wherein the deletion/insertion/substitution is at position 200 in the amino acid sequence shown in SEQ ID NO:1 or at a position corresponding to this position and wherein said variant further has one or more substitutions, deletions and/or insertions in comparison to the corresponding sequence from which it is derived and wherein these substitutions, deletions and/or insertions occur at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

The present invention relates in a preferred embodiment to an HIV kinase variant having an amino acid sequence as shown in SEQ ID NO:1 or an amino acid sequence having at least 70% sequence identity to SEQ ID NO:1, in which one amino acid residue at position 200 in the amino acid sequence shown in SEQ ID NO:1 or at a position corresponding to this position is substituted with another amino acid residue or deleted or wherein an insertion has been effected this position and wherein in said variant one or more further amino acid residues at a position selected from the group consisting of positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1 or at a position corresponding to any of these positions, are substituted with another amino acid residue or deleted or wherein an insertion has been effected at one or more of these positions and wherein said HIV kinase has an improved activity in converting HIV into PIV.

As regards the preferred embodiments of a HIV kinase variant showing an improved activity in converting 3-hydroxyisovalerate (HIV) into 3-phosphonoxyisovalerate (PIV), wherein the HIV kinase variant has a modification at position 200 in the amino acid sequence shown in SEQ ID NO:1 or at a position corresponding to this position and wherein said variant further has one or more substitutions, deletions and/or insertions in comparison to the corresponding sequence from which it is derived, the same applies as has been set forth herein-above.

The present invention also relates to a method for providing a variant of an HIV kinase wherein said variant shows an improved activity of converting 3-hydroxyisovalerate (HIV) into 3-phosphonoxyisovalerate (PIV), said method comprising the step of effecting one or more changes in the sequence of the HIV kinase wherein said change(s) is/are effected at one or more amino acid positions selected from the group consisting of the amino acid positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 200, 202, 203, 205, 206, 208, 211, 217, 240, 248, 252, 256, 259, 260, 285, 289, 295, 296, 302, 303, 307, 311, 313, 315, 316 and 318 in the amino acid sequence shown in SEQ ID NO:1.

"Corresponding to" means corresponding to any of these positions in a related sequence.

As regards the preferred embodiments of an HIV kinase to be mutated according to such a method, the same applies as has been set forth herein-above.

In one preferred embodiment the HIV kinase from which the HIV kinase variant is derived is an HIV kinase which shows the amino acid sequence as shown in SEQ ID NO:1 or an amino acid sequence having at least 70%, 80% or 90% sequence identity to SEQ ID NO:1 or any of the preferred degrees of sequence identity as specified herein above.

Moreover, as regards preferred embodiments of the degree of improvement in activity and the changes to be effected, the same applies as described herein above. The change(s) which is/are effected at any of the above position(s) is/are substitution(s), deletion(s) and/or insertion(s) as defined herein above.

An HIV kinase variant of the present invention can be fused to a homologous or heterologous polypeptide or protein, an enzyme, a substrate or a tag to form a fusion protein. Fusion proteins in accordance with the present invention will have the same improved activity as the alkenol dehydratase of the present invention. Polypeptides, enzymes, substrates or tags that can be added to another protein are known in the art. They may useful for purifying or detecting the proteins of the invention. For instance, tags that can be used for detection and/or purification are e.g. FLAG-tag, His6-tag or a Strep-tag. Alternatively, the protein of the invention can be fused to an enzyme e.g. luciferase, for the detection or localisation of said protein. Other fusion partners include, but are not limited to, bacterial β-galactosidase, trpE, Protein A, β-lactamase, alpha amylase, alcohol dehydrogenase or yeast alpha mating factor. It is also conceivable that the polypeptide, enzyme, substrate or tag is removed from the protein of the invention after e.g. purification. Fusion proteins can typically be made by either recombinant nucleic acid methods or by synthetic polypeptide methods known in art.

The present invention further relates to a nucleic acid molecule encoding an HIV kinase of the present invention and to a vector comprising said nucleic acid molecules. Vectors that can be used in accordance with the present invention are known in the art. The vectors can further comprise expression control sequences operably linked to the nucleic acid molecules of the present invention contained in the vectors. These expression control sequences may be suited to ensure transcription and synthesis of a translatable RNA in bacteria or fungi. Expression control sequences can for instance be promoters. Promoters for use in connection with the nucleic acid molecules of the present invention may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

Preferably, the vector of the present invention is an expression vector. Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

In addition, the present invention relates to a host cell comprising the nucleic acid molecule or the vector of the present invention.

In a preferred embodiment, the host cell according to the presenting invention is a microorganism, in particular a bacterium or a fungus. In a more preferred embodiment, the host cell of the present invention is *E. coli*, a bacterium of the genus *Clostridium* or a yeast cell, such as *S. cerevisiae*. In another preferred embodiment the host cell is a plant cell or a non-human animal cell.

The transformation of the host cell with a vector according to the invention can be carried out by standard methods, as for instance described in Sambrook and Russell (2001), Molecular Cloning: A Laboratory Manual, CSH Press, Cold Spring Harbor, NY, USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to a method for producing PIV from HIV comprising the step of incubating an HIV kinase variant of the invention with HIV under conditions allowing said conversion or comprising the step of culturing a host cell of the present invention in a suitable medium and recovering the produced PIV. It is also conceivable in this context that in such a method not only one enzyme according to the present invention is employed but a combination of two or more enzymes.

The present invention also relates to the use of an HIV kinase variant or a host cell of the present invention as described above for the conversion of HIV into PIV. Moreover, in a further embodiment, the present invention relates to a method for producing PIV from HIV by bringing HIV into contact with the HIV kinase variant of the present invention or with a host cell comprising a vector comprising a nucleic acid molecule encoding the HIV kinase variant of the present invention. Thus, in a preferred embodiment, the present invention relates to a method for converting HIV into PIV comprising the steps of: (i) culturing the above-described host cell of the invention in a suitable medium; and (ii) achieving the production of PIV from HIV.

Thus, in a preferred embodiment, the present invention relates to methods and uses utilizing a host cell of the present invention wherein such a host cell is a recombinant organism in the sense that it is genetically modified due to the introduction of at least one nucleic acid molecule encoding an HIV kinase variant as described above. Preferably, such a nucleic acid molecule is heterologous with regard to the organism which means that it does not naturally occur in said host cell.

In another preferred embodiment, such a host cell is an organism which is capable of producing HIV.

In another preferred embodiment, the method according to the invention is carried out in culture, in the presence of an organism, preferably a microorganism, producing an enzyme variant of the present invention. In such an embodiment of the invention, an organism, preferably a microorganism, that produces an enzyme of the present invention is used. In a preferred embodiment, the (micro)organism is recombinant in that the enzyme produced by the host is heterologous relative to the production host. The method can thus be carried out directly in the culture medium, without the need to separate or purify the enzymes. In an especially advantageous manner, a (micro)organism is used having the natural or artificial property of endogenously producing HIV so as to produce PIV directly from the substrate already present in the culture in solution.

In connection with the above described methods and uses, the microorganisms are cultivated under suitable culture conditions allowing the occurrence of the enzymatic reaction of the HIV variants of the present invention. The specific culture conditions depend on the specific microorganism employed but are well known to the person skilled in the art. The culture conditions are generally chosen in such a manner that they allow the expression of the genes encoding the HIV kinase variant of the present invention. Various methods are known to the person skilled in the art in order to improve and fine-tune the expression of certain genes at certain stages of the culture such as induction of gene expression by chemical inducers or by a temperature shift.

In another embodiment, the above described methods of the invention comprise the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical process like the method of the present invention is carried out which involves organisms, preferably microorganisms and/or biochemically active substances, i.e., the enzyme(s) described above derived from such organisms or organisms harboring the above described enzyme(s). In a bioreactor or a fermenter, this process can either be aerobic or anaerobic. These bioreactors are commonly cylindrical, and may range in size from liters to hundreds of cubic meters, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

In yet a further embodiment, the method according to the invention can be carried out in vitro, e.g. in the presence of isolated enzyme or of cell lysates comprising the enzyme or partially purified enzyme preparations comprising the HIV kinase variant of the present invention. In vitro preferably means in a cell-free system.

In one embodiment, the enzyme employed in the method is used in purified form. However, such a method may be costly, since enzyme and substrate production and purification costs are high.

Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

In an in vitro reaction the enzymes, native or recombinant, purified or not, are incubated in the presence of the substrate in physicochemical conditions allowing the enzymes to be active, and the incubation is allowed to proceed for a sufficient period of time allowing production of the desired product as described above. At the end of the incubation, one optionally measures the presence of PIV by using any detection system known to one of skill in the art such as gas chromatography or colorimetric tests for measuring the formation of PIV and/or isobutene.

In a particularly preferred embodiment of the invention the method is carried out in vitro and the enzyme is immobilized. Means and methods for immobilizing enzymes on different supports are well-known to the person skilled in the art.

In another preferred embodiment, the present invention relates to a method for producing isobutene (IBN) from HIV comprising the method for producing PIV from HIV by contacting HIV with the HIV kinase variant as described herein above (or with a host cell expressing the HIV kinase variant as described herein above, i.e., a host cell comprising a nucleic acid molecule encoding the HIV kinase variant of the present invention as described herein above or a vector comprising such a nucleic acid molecule) and further the step of converting the thus produced PIV into IBN by a dephosphorylation/decarboxylation reaction.

There are basically three ways how the produced PIV can be converted into IBN according to the present invention.

First, PIV is produced from HIV by contacting HIV with the HIV kinase variant as described herein above (or with a host cell expressing the HIV kinase variant as described herein above, i.e., a host cell comprising a nucleic acid molecule encoding the HIV kinase variant of the present invention as described herein above or a vector comprising such a nucleic acid molecule). In a subsequent step, the temperature is increased, and, accordingly, PIV is spontaneously dephosphorylated/decarboxylated into IBN. It has previously been demonstrated that when, e.g., the temperature of the reaction is increased from 30° C. to 50° C., PIV is spontaneously decarboxylated into IBN. Thus, in a preferred embodiment, in the methods of the present invention, the temperature of the reaction is increased to up to 40° C., 45° C., 50° C., 55° C., 60° C. or up to 70° C.

Second, PIV is produced from HIV comprising the method for producing PIV from HIV by contacting HIV with the HIV kinase variant as described herein above (or with a host cell expressing the HIV kinase variant as described herein above, i.e., a host cell comprising a nucleic acid molecule encoding the HIV kinase variant of the present invention as described herein above or a vector comprising such a nucleic acid molecule) wherein this reaction is performed at increased temperatures as described above which concomitantly allow the thus produced PIV to be spontaneously decarboxylated into IBN. This can, e.g., be achieved with a thermostable/thermoresistant host cell, preferably a thermostable/thermoresistant bacterium, which is stable at the above increased temperatures and capable of growing and surviving at the above increased temperatures. Thermostable/thermoresistant host cells, preferably thermostable/thermoresistant bacteria, are known to the skilled person.

Third, the produced PIV can be converted into IBN according to the present invention in a subsequent reaction as follows.

It has been described previously that certain MDP decarboxylases show a high activity in the conversion of PIV into IBN (WO2012/052427). Thus, in a preferred embodiment, the resulting PIV can be decarboxylated by a protein from the MDP family (EC 4.1.1.33). Moreover, mevalonate diphosphate decarboxylase variants having improved activity in converting 3-phosphonoxyisovalerate into isobutene have previously been described (WO2015/004211). Therefore, the present invention also relates to the use of an MDP decarboxylase or of a mevalonate diphosphate decarboxylase variant as described in WO2012/052427 and WO2015/004211, respectively, or of a microorganism expressing such an enzyme or a variant thereof for the conversion of the thus produced PIV into IBN by a dephosphorylation/decarboxylation reaction.

The method according to the invention furthermore comprises the step of collecting gaseous products, i.e. isobutene, degassing out of the reaction, i.e. recovering the product which degasses, e.g., out of the culture. Thus, in a preferred embodiment, the method is carried out in the presence of a system for collecting isobutene under gaseous form during the reaction.

As a matter of fact, isobutene adopts the gaseous state at room temperature and atmospheric pressure. Moreover, isobutene also adopts the gaseous state under culture conditions at 37° C. The method according to the invention therefore does not require extraction of isobutene from the liquid culture medium, a step which is always very costly when performed at industrial scale. The evacuation and storage of gaseous hydrocarbons, in particular of isobutene, and their possible subsequent physical separation and chemical conversion can be performed according to any method known to one of skill in the art.

In addition, the present invention also relates to a method for producing PIV from HIV or for producing IBN from HIV as described herein above wherein the method further comprises providing the HIV by the enzymatic conversion of acetone into said HIV. The production of HIV from acetone has previously been described wherein, in a condensation reaction, acetone and acetyl-CoA are reacted by an HMG-CoA synthase to form HIV (WO2011/032934). Further, variants derived from the *Mus musculus* HMG-CoA synthase have been described having improved capabilities in condensing acetone and acetyl-CoA into HIV (WO2015/101493). Thus, the present invention also relates to the use of an HMG-CoA synthase or a variant thereof as described in WO2011/032934 and WO2015/101493, respectively, or of a microorganism expressing such an enzyme or a variant thereof in a method for producing PIV from HIV or for producing IBN from HIV as described herein above wherein the method further comprises providing the HIV by the enzymatic conversion of acetone into said HIV. Accordingly, in such a method, the HIV produced from acetone and acetyl-CoA (catalyzed by either an HMG-CoA synthase or a variant thereof) may then form the starting molecule for the above two step reaction, i.e., the activation by an ATP-dependent phosphorylation resulting in 3-phosphonoxyisovalerate (PIV) which, in an optional second step, is decarboxylated into isobutene.

Finally, the present invention relates to a composition comprising a variant of an HIV kinase of the present invention, a nucleic acid molecule of the present invention, a vector of the present invention or a host cell of the present invention. As regards the variant of an HIV kinase, the nucleic acid molecule, the vector or the host cell, the same applies as has been set forth above in connection with the methods according to the present invention.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

FIG. 1: shows a two-step pathway for the decarboxylation of 3-hydroxyisovalerate (HIV) into isobutene. HIV is first phosphorylated into 3-phosphonoxyisovalerate (PIV). PIV is then dephosphorylated/decarboxylated into isobutene.

Figure 2:
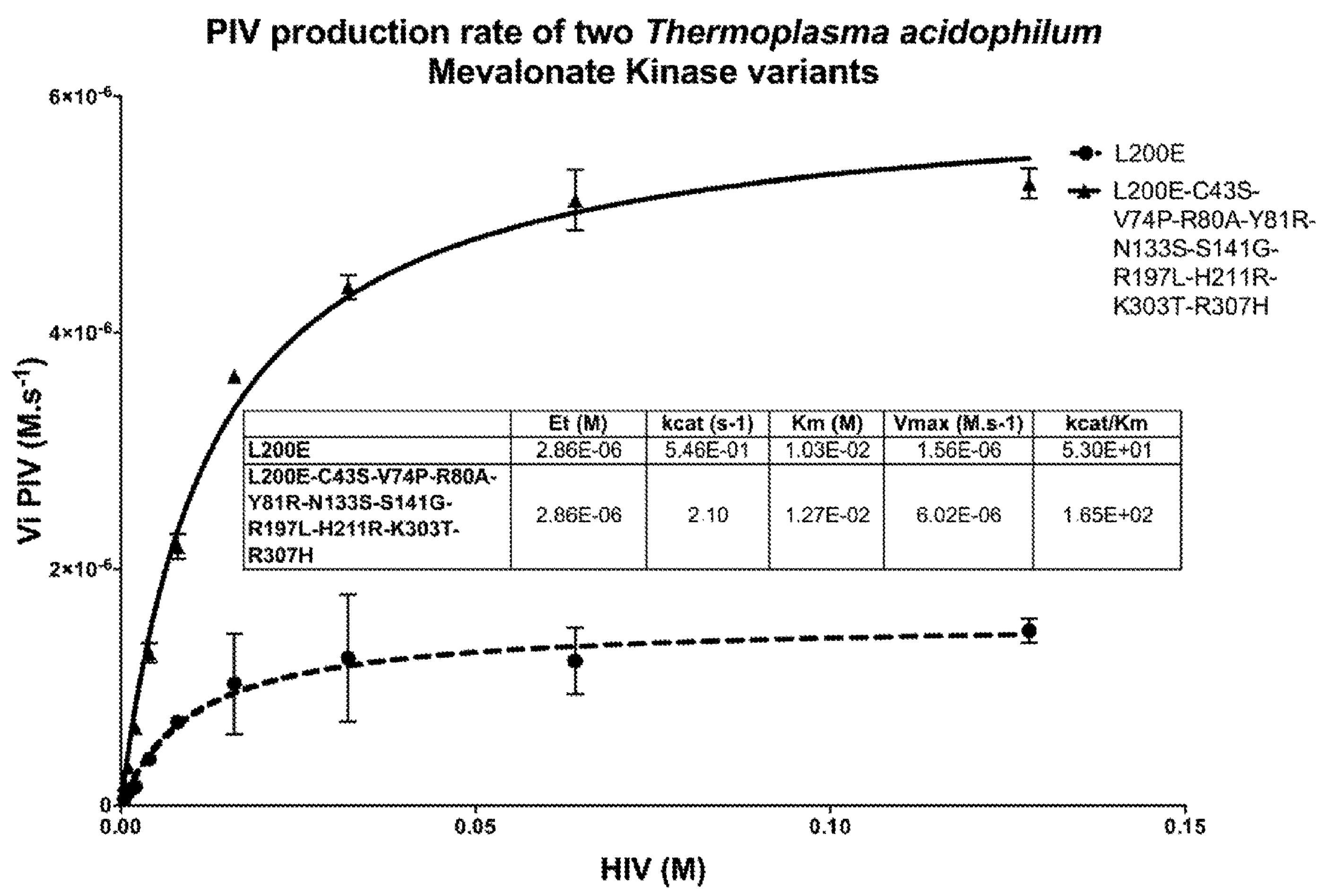

FIG. 2: 3-phosphonoxyisovalerate (PIV) production rate of two *Thermoplasma acidophilum* mevalonate kinase variants as a function of 3-hydroxyisovalerate (HIV) concentration. Knowing the concentration Et of each enzyme, the Michaelis-Menten approximation is used to fit the experimental data in order to compute the Michaelis constant Km, the maximum production rate Vm, the catalytic rate constant kcat and the catalytic efficiency (kcat/Km).

The invention will now be described by reference to the following examples which are merely illustrative and are not to be construed as a limitation of the scope of the present invention.

EXAMPLES

Example 1

Directed Evolution Strategy

The enzyme *Thermoplasma acidophilum* mevalonate kinase (SEQ ID NO:1) is capable of catalysing, amongst other reactions, the phosphorylation of 3-hydroxyisovalerate (HIV) into 3-phosphonoxyisovalerate (PIV) as described in WO2012052427. A directed evolution approach was used in order to specifically improve the catalytic efficiency of this reaction. This approach consisted in (1) the design of assay systems to test the activity of enzyme variants, (2) the generation of collections of single point or multiple mutants for *T. acidophilum* mevalonate kinase, (3) the use of the activity assays to screen the collection of mutants in order to identify with improved activity compared to the activity of the wild type *T. acidophilum* mevalonate kinase. Different cycles of evolution are repeated several times (steps (2) and (3)) using improved variants as the new seed for the generation of new variants.

This approach led to the identification and characterization of a collection of mutants with increased activity compared to the wild type enzyme.

Example 2

Construction of *Thermoplasma acidophilum* Mevalonate Kinase Enzyme Mutants

The polynucleotide sequences coding for the different mutants identified during the evolution of the *Thermoplasma acidophilum* mevalonate kinase enzyme were generated using a range of standard molecular biology techniques. All these techniques used a codon-optimised polynucleotide sequence for expression in *Escherichia coli* as template. The sequence optimisation has been done by Geneart using their GeneOptimizer software.

Different PCR-based techniques known in the art were used for the construction of single-point mutants. For the generation of enzyme variants bearing multiple mutations (at least two mutations), either PCR-based techniques or other methods known in the art were used to introduce these mutations.

Following mutagenesis, the mutated polynucleotide sequence was inserted into an expression vector (used for recombinant protein production in *E. coli* and screening) either using standard ligase-based subcloning techniques, whole plasmid extension by PCR or ligase-independent cloning techniques.

Example 3

Methods for the Identification of the Enzyme Mutants with Increased Activity Three different screening methods were developed and used during the evolution of the *Thermoplasma acidophilum* mevalonate kinase enzyme which are summarized in the following.

1) In Vitro Coupled Assay on a HIV Substrate Substrate (IN VITRO)

The *Thermoplasma acidophilum* mevalonate kinase enzyme variants were cloned in the pET 25b vector (Novagen). A stretch of 6 histidine codons was inserted after the methionine initiation codon to provide an affinity tag for purification. Competent *E. coli* BL21 (DE3) cells (Novagen) were transformed in 96-well plates with these vectors according to the heat shock procedure and plated out onto LB-agar plates supplemented with the appropriate antibiotic. Cells were grown overnight at 30° C. until individual colonies reach the desired size. Single colonies were then picked and individually transferred into 500 μL of liquid LB medium supplemented with the appropriate antibiotic. Cell growth is carried out with shaking for 20 hours at 30° C. The LB cultures were used to inoculate 1 mL of of auto-induction medium (Studier F W, Prat. Exp. Pur. 41, (2005), 207-234) supplemented with the appropriate antibiotic and grown in a shaking incubator set at 1000 rpm and 85% humidity for 6 h at 37° C. and protein expression was continued at 28° C. overnight (approximately 16 h). The cells were collected by centrifugation at 4° C., 10,000 rpm for 20 min and the pellets were frozen at −80° C. The pellets were thawed on ice and resuspended in 200 μL ml of BugBuster (Millipore) and one microliter of lysonase (Novagen) was added. Cells were incubated 10 minutes at room temperature and then returned to ice for 20 minutes. The bacterial extracts were then clarified by centrifugation at 4° C., 10,000 rpm for 20 min. The clarified bacterial lysates were loaded on Protino multi-96 Ni-IDA microplates (Macherey-Nagel) allowing adsorption of 6-His tagged proteins. Columns were washed and the enzymes of interest were eluted with 400 μL of the supplied elution buffer. Eluates were then concentrated by centrifugation, washing and resuspension in 120 μL of 50 mM Tris/HCl pH 7. Protein concentrations were quantified using a Nanodrop 1000 (ThermoScientific).

*Thermoplasma acidophilum* mevalonate kinase phosphorylates HIV into PIV by an ATP to ADP conversion. It is thus possible to follow the rate of conversion of HIV into PIV by measuring the production of ADP, by assays known to the person skilled in the art. The release of ADP was quantified using a pyruvate kinase/lactate dehydrogenase coupled assay. Briefly, in the presence of ADP and the pyruvate kinase (PK), phosphoenolpyruvate (PEP) is converted into pyruvate, which is then converted into lactate by the lactate dehydrogenase (LDH). This last reaction requires a molecule of NADH which is oxidised in $NAD_+$. The rate of NADH oxidation, proportional to the ADP production, is followed by the rate of absorbance decrease at 340 nm. The enzymatic reaction is carried out at 40° C. in a 50 mM Tris-HCl pH7 buffer, with 10 mM MgCl2, 100 mM KCl, 0.4 mM NADH, 1 mM PEP, 1.5 U/mL PK and 3 U/mL LDH, 5 mM ATP, the mevalonate kinase variant at 0.05 mg/mL and different concentrations of HIV ranging from 0 to 20 mM. By following the absorbance at 340 nm, an initial velocity of conversion can be calculated and using the Michaelis-Menten approximation, the enzyme catalytic efficiency can be computed.

2) In Vivo Coupled Assay on an Acetone Substrate (IN VIVO 1)

For the in vivo testing a screening assay was developed. This coupled assay is based on the use of a bacterial strain transformed with an expression vector that contains the coding sequences and lead to the production of three enzymes involved in a three-step metabolic pathway converting acetone to isobutene.

In this pathway, the first step is the production of 3-hydroxyisovalerate (HIV) from acetone. Condensation of acetone and acetyl-CoA into 3-hydroxyisovalerate by HMG-CoA Synthases has been described previously (WO2011032934). In this study, variants of the *Mus musculus* HMG-CoA Synthase (referred to in the following as "HIV synthase") were used. Variants of HIV synthase have previously been described in WO2015/101493. In this assay, acetone is exogenously provided while acetyl-CoA is provided by the *E. coli* strain. The second step is the phosphorylation of HIV into PIV. The *Thermoplasma acidophilum* mevalonate kinase variants were used to catalyze this step. The third step is the decarboxylation of 3-phosphonoxyisovalerate into isobutene (IBN), catalyzed by a mevaonate diphosphate decarboxylase, as described in WO2012052427. Variants of the *Streptococcus mitis* MDP decarboxylase (referred to in the following as PIV decarboxylase), described in WO2015004211, were used.

This strain is first plated out onto LB-agar plates supplemented with the appropriate antibiotic. Cells were grown overnight at 30° C. until individual colonies reach the desired size. Single colonies were then picked and individually transferred into either 50 or 500 μL of liquid LB medium supplemented with the appropriate antibiotic. Cell growth is carried out with shaking for 20 hours at 30° C. The LB cultures were used to inoculate 300 μL in 384 deepwell microplates or 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the three types of recombinant enzymes. The cell pellet containing these three overexpressed recombinant enzymes is then resuspended in 50 μL (or 500 μL) of minimum medium supplemented with 250 mM or 500 mM acetone and incubated for a further 16 hours in a shaking incubator at 37° C., 700 rpm. During this step, HIV synthase catalyses the condensation of acetone with the cellular acetyl-CoA into HIV, which is then converted into PIV by the *Thermoplasma acidophilum* mevalonate kinase variants tested. The PIV decarboxylase finally catalyses the conversion of PIV into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL/min constant flow of nitrogen as carrier gas. Upon injection, peak areas of isobutene were calculated.

3) In Vivo Assay Based on Exogenous HIV (IN VIVO 2)

A second in vivo screening assay was developed. This assay is based on the use of a bacterial strain transformed with an expression vector that contain the coding sequences and lead to the production of the last two enzymes involved in a metabolic pathway converting HIV to isobutene. The reactions involved in this pathway are the two last reactions of the pathway used in the IN VIVO 1 assay: phosphorylation of HIV into PIV and decarboxylation of PIV into isobutene. The same enzymes were used as for the IN VIVO 1 assay.

This strain is first plated out onto LB-agar plates supplemented with the appropriate antibiotic. Cells were grown overnight at 30° C. until individual colonies reach the desired size. Single colonies were then picked and individually transferred into 50 μl of liquid LB medium supplemented with the appropriate antibiotic. Cell growth is carried out with shaking for 20 hours at 30° C. The LB cultures were used to inoculate 300 μL in 384 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the two types of recombinant enzymes. The cell pellet containing these two overexpressed recombinant enzymes is then resuspended in 30 μL of minimum medium supplemented with 10 mM HIV and incubated for a further 4 or 16 hours in a shaking incubator at 37° C., 700 rpm. During this step, the *Thermoplasma acidophilum* mevalonate kinase variants catalyse the phosphorylation of HIV into PIV. The PIV decarboxylase finally catalyses the conversion of PIV into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL/min constant flow of nitrogen as carrier gas. Upon injection, peak areas of isobutene were calculated.

4) Selection Based Assays (SELECTION 1 and SELECTION 2)

In order to efficiently select improved variants from the high diversity libraries and filter out non-working variants, a negative selection assay was designed. It has been shown that, in the presence of HIV in the culture medium, the growth rate of a strain was inversely proportional to the *Thermoplasma acidophilum* mevalonate kinase variant catalytic efficiency. This property was used for selecting the best active/best performing variants using the following protocol.

The *Thermoplasma acidophilum* mevalonate kinase enzyme variants were cloned in the pET 25b vector (Novagen). Competent *E. coli* BL21 (DE3) cells (Novagen) were transformed in 96-well plates with these vectors according to the heat shock procedure and plated out onto LB-agar plates supplemented with the appropriate antibiotic. Cells were grown overnight at 30° C. until individual colonies reach the desired size. Single colonies were then picked and individually transferred into 1200 μL of liquid LB medium supplemented with the appropriate antibiotic. Cell growth is carried out with shaking for 22 hours at 30° C. The LB cultures were used to inoculate 150 μL of selection medium (LB, appropriate antibiotic, 0.1 mM IPTG, 10 mM HIV) and grown in a shaking incubator set at 700 rpm and 85% humidity for 5 h at 30° C. The optical density (OD) of each well is measured and compared against a reference. Only the wells presenting an OD inferior to the reference are chosen. The variants then selected are either tested directly according to the in vitro assay described in 1) or subcloned into the appropriate vector and screened according to the in vivo assay described in 3). The selected variants are summarized in the below Tables as results of these selection-based assays SELECTION 1 and SELECTION 2, respectively.

5) In Vivo Assay Based on Exogenous HIV (IN VIVO 3)

A third in vivo screening assay was developed. This assay is based on the use of a bacterial strain transformed with an expression vector that contains the coding sequences and lead to the production of the last two enzymes involved in the metabolic pathway converting HIV to isobutene; namely the *Thermoplasma acidophilum* mevalonate kinase variants were used for the phosphorylation of HIV into PIV and the above-mentioned *Streptococcus mitis* MDP decarboxylase was used for the conversion of 3-phosphonoxyisovalerate into isobutene (IBN) (referred to in the following as PIV decarboxylase).

This strain is first plated out onto LB-agar plates supplemented with the appropriate antibiotic. Cells were grown overnight at 30° C. until individual colonies reached the desired size. Single colonies were then picked and individually transferred into 200 μL of liquid LB medium supplemented with the appropriate antibiotic. Cell growth is carried out with shaking for 20 hours at 30° C. The LB cultures were used to inoculate 1400 μL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the two types of recombinant enzymes. The cell pellet containing these two overexpressed recombinant enzymes was then resuspended in 400 μL of minimum medium supplemented with 10 mM HIV and incubated for a further 1 or 2 hours in a shaking incubator at 30° C., 700 rpm. During this step, the *Thermoplasma acidophilum* mevalonate kinase variants catalyse the phosphorylation of HIV into PIV. The PIV decarboxylase finally catalyses the conversion of PIV into IBN. After 5 min inactivation at 80° C., the IBN produced is quantified by gas chromatography as follows. 100 μL of headspace gases from each enzymatic reaction were injected in a Brucker GC-450 system equipped with a Flame Ionization Detector (FID). Compounds present in samples were separated by chromatography using a RTX-1 columns at 100° C. with a 1 mL.min-1 constant flow of nitrogen as carrier gas. Upon injection, peak areas of isobutene were calculated.

Example 4

Identification of Variants of *Thermoplasma acidophilum* Mevalonate Kinase with further Increased Activity for the Reaction of Conversion of 3-hydroxyisovalerate into 3-phosphonoxyisovalerate A collection of single-point mutants and multiple mutants was created by successive rounds of mutagenesis, recombination of single and multiple mutations, using the *Thermoplasma acidophilum* mevalonate kinase (SEQ ID NO:1) as the template. Several variants with an enhanced activity in converting 3-hydroxyisovalerate into 3-phosphonoxyisovalerate have been identified through in vitro and/or in vivo screening assays as described above. The increase in activity is described relative to the wild-type enzyme (with "+" representing a low increase in activity and "++++++" and up to "+++++++" representing a high increase in activity). The activity considered is the increased production of 3-phosphonoxyisovalerate from 3-hydroxyisovalerate as measured directly (see the above-described "IN VITRO" and "SELECTION" assays), through the successive conversion of acetone to 3-hydroxyisovalerate, subsequently to 3-phosphonoxyisovalerate and finally to isobutene (see the above-described "IN VIVO 1" assay) or by the combined conversion of 3-hydroxyisovalerate into isobutene (through 3-phosphonoxyisovalerate) (see the above-described "IN VIVO 2" and "IN VIVO 3" assay). The list of these variants is presented in the following Table 1, the list of individual mutations in Table 2 and the list of the positions presenting an increase in activity, either as single-point mutations or in combination with others, is presented in Table 3.

TABLE 1

List of *Thermoplasma acidophilum* mevalonate kinase variants presenting an increase in 3-phosphonoxyisovalerate production from 3-hydroxyisovalerate

| Mutations | Activity relative to the wild-type enzyme | Screening Assay used |
|---|---|---|
| E252S | + | IN VITRO |
| H59R | + | IN VITRO |
| I6L | + | IN VITRO |
| L200E | + | IN VITRO |
| L200E-I6L | + | IN VITRO |
| L200E-S240G | + | IN VITRO |
| L200T | + | IN VITRO |
| S240G | + | IN VITRO |
| V26F | + | IN VITRO |
| L200E-A137S | ++ | IN VIVO 2 |
| L200E-E285C | ++ | IN VIVO 1 |
| L200E-E49D-V77P-R315K | ++ | IN VIVO 1 |
| L200E-E49S-V74P | ++ | IN VIVO 1 |
| L200E-F89G | ++ | IN VIVO 2 |
| L200E-G90P | ++ | IN VIVO 2 |
| L200E-H211K | ++ | IN VIVO 1 |
| L200E-H211R | ++ | IN VIVO 1 |
| L200E-L135C | ++ | IN VIVO 1 |
| L200E-P25R | ++ | IN VIVO 1 |
| L200E-R197K | ++ | IN VIVO 1 |
| L200E-R197L | ++ | IN VIVO 1 |
| L200E-R307H | ++ | IN VIVO 2 |
| L200E-R315K | ++ | IN VIVO 1 |
| L200E-R76P | ++ | IN VIVO 1 |
| L200E-S67N-R197K | ++ | IN VIVO 1 |
| L200E-S73P-V74P | ++ | IN VIVO 2 |
| L200E-S82D | ++ | IN VIVO 1 |
| L200E-V74P | ++ | IN VIVO 1 |
| L200E-V74P-A137P | ++ | IN VIVO 2 |
| L200E-V74P-E285C | ++ | IN VIVO 1 |
| L200E-V74P-F89S | ++ | IN VIVO 2 |
| L200E-V74P-G90P-T91S | ++ | IN VIVO 2 |

TABLE 1-continued

List of *Thermoplasma acidophilum* mevalonate kinase variants presenting an increase in 3-phosphonoxyisovalerate production from 3-hydroxyisovalerate

| Mutations | Activity relative to the wild-type enzyme | Screening Assay used |
|---|---|---|
| L200E-V74P-G90S-T91G | ++ | IN VIVO 2 |
| L200E-V74P-G90S-T91P | ++ | IN VIVO 2 |
| L200E-V74P-G90S-T91S | ++ | IN VIVO 2 |
| L200E-V74P-H211K | ++ | IN VIVO 1 |
| L200E-V74P-H211R | ++ | IN VIVO 1 |
| L200E-V74P-L135C | ++ | IN VIVO 1 |
| L200E-V74P-R136G | ++ | IN VIVO 2 |
| L200E-V74P-R197L | ++ | IN VIVO 1 |
| L200E-V74P-R315H | ++ | IN VIVO 1 |
| L200E-V74P-R315K | ++ | IN VIVO 1 |
| L200E-V74P-T91G | ++ | IN VIVO 2 |
| L200E-V74P-T91P | ++ | IN VIVO 2 |
| L200E-V74P-T91S | ++ | IN VIVO 2 |
| L200E-V74P-W313T | ++ | IN VIVO 1 |
| L200E-V77P | ++ | IN VIVO 1 |
| L200E-V77P-H211R | ++ | IN VIVO 1 |
| L200E-V77P-R197L | ++ | IN VIVO 1 |
| L200E-V77P-R315H | ++ | IN VIVO 1 |
| L200E-V77P-R315K | ++ | IN VIVO 1 |
| L200E-V77P-W313R | ++ | IN VIVO 1 |
| L200E-V77P-W313T | ++ | IN VIVO 1 |
| L200E-V77P-W313Y | ++ | IN VIVO 1 |
| L200E-W313R | ++ | IN VIVO 1 |
| L200E-W313T | ++ | IN VIVO 1 |
| L200E-W313Y | ++ | IN VIVO 1 |
| L200E-Y81E | ++ | IN VIVO 1 |
| L200E-Y81T | ++ | IN VIVO 1 |
| L200E-R76P-L135C-R197L-H211R | +++ | IN VIVO 1 |
| L200E-R76P-Y81T-L135C-R197L-H211R | +++ | IN VIVO 1 |
| L200E-R76P-Y81T-R197L-H211R | +++ | IN VIVO 1 |
| L200E-V74P-V77P-H211K | +++ | IN VIVO 1 |
| L200E-V74P-V77P-H211R | +++ | IN VIVO 1 |
| L200E-V74P-V77P-L135C-R197L-H211R | +++ | IN VIVO 1 |
| L200E-V74P-V77P-R197L-H211R | +++ | IN VIVO 1 |
| L200E-V77P-H211K-W313T | +++ | IN VIVO 1 |
| L200E-V77P-L135C-H211K | +++ | IN VIVO 1 |
| L200E-V77P-L135C-H211R | +++ | IN VIVO 1 |
| L200E-V77P-R197C-H211R | +++ | IN VIVO 1 |
| L200E-V77P-V94S-L135C-R197L-H211R | +++ | IN VIVO 1 |
| L200E-L135C-H211R-R76P-Y81T-R197L | ++++ | IN VIVO 1 |
| L200E-V77P-L135C-H211R-R197L-R80A-Y81R | ++++ | IN VIVO 1 |
| L200E-V77P-L135C-H211R-R80A-Y81Q | ++++ | IN VIVO 1 |
| L200E-V77P-L135C-H211R-R80A-Y81R | ++++ | IN VIVO 1 |
| L200E-V77P-L135C-H211R-R80T-Y81R | ++++ | IN VIVO 1 |
| L200E-V77P-L135C-H211R-S141A | ++++ | IN VIVO 1 |
| L200E-V77P-L135C-H211R-S141G | ++++ | IN VIVO 1 |
| L200E-V77P-L135C-H211R-T65D | ++++ | IN VIVO 1 |
| L200E-V77P-L135C-H211R-T65E | ++++ | IN VIVO 1 |
| L200E-V77P-L135C-H211R-V74P-R197L | ++++ | IN VIVO 1 |
| L200E-V77P-L135C-H211R-V74P-R197L-R80A-Y81R | ++++ | IN VIVO 1 |
| L200E-V77P-L135C-H211R-V74P-R197L-R80T-Y81R | ++++ | IN VIVO 1 |
| L200E-V77P-L135C-H211R-V74P-R80T-Y81R | ++++ | IN VIVO 1 |
| L200E-V77P-L135C-H211R-Y183D | ++++ | IN VIVO 1 |
| L200E-V77P-L135C-H211R-Y3H | ++++ | IN VIVO 1 |
| L200E-V74P-R197L-H211R-E49G-T91S | +++++ | IN VIVO 2 |
| L200E-V74P-R197L-H211R-G90P-T91S-L135C-A137P | +++++ | IN VIVO 2 |
| L200E-V74P-R197L-H211R-H32D-S73P-Y81R-G90S-T91S-L135C-R136G | +++++ | IN VIVO 2 |
| L200E-V74P-R197L-H211R-L135C | +++++ | IN VIVO 2 |
| L200E-V74P-R197L-H211R-R80A-G90S-T91G-R307H | +++++ | IN VIVO 2 |
| L200E-V74P-R197L-H211R-R80A-L135C-R307H | +++++ | IN VIVO 2 |
| L200E-V74P-R197L-H211R-R80A-T91G-R307H | +++++ | IN VIVO 2 |
| L200E-V74P-R197L-H211R-R80A-Y81R-T91G | +++++ | IN VIVO 2 |
| L200E-V74P-R197L-H211R-S73P-Y81R-L135C | +++++ | IN VIVO 2 |
| L200E-V74P-R197L-H211R-Y81R-A137S | +++++ | IN VIVO 2 |
| L200E-V74P-R197L-H211R-Y81R-G90S-T91S-R307H | +++++ | IN VIVO 2 |
| L200E-V74P-R197L-H211R-Y81R-G90S-T91S-T93I-L135C-R307H | +++++ | IN VIVO 2 |
| L200E-V74P-R197L-H211R-Y81R-L135C-R307H | +++++ | IN VIVO 2 |
| L200E-V74P-R197L-H211R-Y81R-T91G-A137S-R307H | +++++ | IN VIVO 2 |
| L200E-V77P-L135C-H211R-V74P-R80A-Y81R-R197L-A137E | +++++ | SELECTION 2 |
| L200E-V77P-L135C-H211R-V74P-R80A-Y81R-R197L-A208T | +++++ | SELECTION 1 |

TABLE 1-continued

List of *Thermoplasma acidophilum* mevalonate kinase variants presenting an increase in 3-phosphonoxyisovalerate production from 3-hydroxyisovalerate

| Mutations | Activity relative to the wild-type enzyme | Screening Assay used |
|---|---|---|
| L200E-V77P-L135C-H211R-V74P-R80A-Y81R-R197L-A23T-V94A-K123N | +++++ | SELECTION 2 |
| L200E-V77P-L135C-H211R-V74P-R80A-Y81R-R197L-C43S | +++++ | SELECTION 2 |
| L200E-V77P-L135C-H211R-V74P-R80A-Y81R-R197L-D70V-A88T-K92T | +++++ | SELECTION 2 |
| L200E-V77P-L135C-H211R-V74P-R80A-Y81R-R197L-F158S | +++++ | SELECTION 1 |
| L200E-V77P-L135C-H211R-V74P-R80A-Y81R-R197L-G121A-S259N | +++++ | SELECTION 1 |
| L200E-V77P-L135C-H211R-V74P-R80A-Y81R-R197L-G44D | +++++ | SELECTION 2 |
| L200E-V77P-L135C-H211R-V74P-R80A-Y81R-R197L-G44D-K205I | +++++ | SELECTION 2 |
| L200E-V77P-L135C-H211R-V74P-R80A-Y81R-R197L-G7V-S45I-E49D-S67C-A160V-K303T | +++++ | SELECTION 2 |
| L200E-V77P-L135C-H211R-V74P-R80A-Y81R-R197L-I46V | +++++ | SELECTION 2 |
| L200E-V77P-L135C-H211R-V74P-R80A-Y81R-R197L-K256R-K302R | +++++ | SELECTION 2 |
| L200E-V77P-L135C-H211R-V74P-R80A-Y81R-R197L-K303T | +++++ | SELECTION 2 |
| L200E-V77P-L135C-H211R-V74P-R80A-Y81R-R197L-N133S | +++++ | SELECTION 2 |
| L200E-V77P-L135C-H211R-V74P-R80A-Y81R-R197L-N24D | +++++ | SELECTION 1 |
| L200E-V77P-L135C-H211R-V74P-R80A-Y81R-R197L-N24D-S141A-Q184P-A208T | +++++ | IN VIVO 1 |
| L200E-V77P-L135C-H211R-V74P-R80A-Y81R-R197L-P25L-N71I-F147L-K302R | +++++ | SELECTION 2 |
| L200E-V77P-L135C-H211R-V74P-R80A-Y81R-R197L-Q184P | +++++ | SELECTION 1 |
| L200E-V77P-L135C-H211R-V74P-R80A-Y81R-R197L-Q99K | +++++ | SELECTION 2 |
| L200E-V77P-L135C-H211R-V74P-R80A-Y81R-R197L-S141A | +++++ | IN VIVO 1 |
| L200E-V77P-L135C-H211R-V74P-R80A-Y81R-R197L-S141G | +++++ | IN VIVO 1 |
| L200E-V77P-L135C-H211R-V74P-R80A-Y81R-R197L-S141G-Q184P-A208T | +++++ | IN VIVO 1 |
| L200E-V77P-L135C-H211R-V74P-R80A-Y81R-R197L-S83N-I295N | +++++ | SELECTION 2 |
| L200E-V77P-L135C-H211R-V74P-R80A-Y81R-R197L-S8T-I115V | +++++ | SELECTION 2 |
| L200E-V77P-L135C-H211R-V74P-R80A-Y81R-R197L-T65E | +++++ | IN VIVO 1 |
| L200E-V77P-L135C-H211R-V74P-R80A-Y81R-R197L-T65E-S141A-Q184P-A208T | +++++ | IN VIVO 1 |
| L200E-V77P-L135C-H211R-V74P-R80A-Y81R-R197L-Y260H | +++++ | SELECTION 2 |
| L200E-V74P-R197L-H211R-C43S-G44D-R80A-Y81R-N133S-S141G-Y260H-R307H | ++++++ | IN VIVO 2 |
| L200E-V74P-R197L-H211R-C43S-L135C-S141G | ++++++ | IN VIVO 2 |
| L200E-V74P-R197L-H211R-C43S-Q99K-N133S-L135C-R136G-S141A-K303T | ++++++ | IN VIVO 2 |
| L200E-V74P-R197L-H211R-C43S-Q99K-N133S-L135C-R136G-S141G-K303T-R307H | ++++++ | IN VIVO 2 |
| L200E-V74P-R197L-H211R-C43S-Q99K-N133S-L135C-R136G-S141G-Y260H-K303T-R307H | ++++++ | IN VIVO 2 |
| L200E-V74P-R197L-H211R-C43S-Q99K-N133S-S141G-Y260H-K303T | ++++++ | IN VIVO 2 |
| L200E-V74P-R197L-H211R-C43S-R80A-Q99K-L135C-S141G-R307H | ++++++ | IN VIVO 2 |
| L200E-V74P-R197L-H211R-C43S-R80A-Q99K-N133S-L135C-S141G-K303T | ++++++ | IN VIVO 2 |
| L200E-V74P-R197L-H211R-C43S-R80A-Q99K-N133S-S141G-Y260H-K303T | ++++++ | IN VIVO 2 |
| L200E-V74P-R197L-H211R-C43S-R80A-T91S-Q99K-L135C-R136G-S141G-K303T | ++++++ | IN VIVO 2 |
| L200E-V74P-R197L-H211R-C43S-R80A-Y81R-N133S-S141G-K303T-R307H | ++++++ | IN VIVO 2 |
| L200E-V74P-R197L-H211R-C43S-R80A-Y81R-Q99K-N133S-S141G-K303T | ++++++ | IN VIVO 2 |
| L200E-V74P-R197L-H211R-C43S-R80A-Y81R-T91S-Q99K-L135C-R136G-S141G-Y260H-K303T | ++++++ | IN VIVO 2 |
| L200E-V74P-R197L-H211R-C43S-R80A-Y81R-T91S-Q99K-L135C-S141A-Y260H-K303T | ++++++ | IN VIVO 2 |
| L200E-V74P-R197L-H211R-C43S-R80A-Y81R-T91S-Q99K-N133S-L135C-R136G-S141G-Y260H-K303T | ++++++ | IN VIVO 2 |
| L200E-V74P-R197L-H211R-C43S-S141G-R307H | ++++++ | IN VIVO 2 |
| L200E-V74P-R197L-H211R-C43S-T91S-N133S-S141G-Y260H-K303T | ++++++ | IN VIVO 2 |
| L200E-V74P-R197L-H211R-C43S-Y81R-L135C-R136G-S141G-Y260H-K303T | ++++++ | IN VIVO 2 |

TABLE 1-continued

List of *Thermoplasma acidophilum* mevalonate kinase variants presenting an increase in 3-phosphonoxyisovalerate production from 3-hydroxyisovalerate

| Mutations | Activity relative to the wild-type enzyme | Screening Assay used |
|---|---|---|
| L200E-V74P-R197L-H211R-C43S-Y81R-Q99K-N133S-S141G-Y260H-K303T | ++++++ | IN VIVO 2 |
| L200E-V74P-R197L-H211R-C43S-Y81R-S141G-E252K-Y260H-R307H | ++++++ | IN VIVO 2 |
| L200E-V74P-R197L-H211R-C43S-Y81R-S141G-Y260H-K303T | ++++++ | IN VIVO 2 |
| L200E-V74P-R197L-H211R-C43S-Y81R-T91S-L135C-S141A-Y260H-K303T | ++++++ | IN VIVO 2 |
| L200E-V74P-R197L-H211R-C43S-Y81R-T91S-N133S-R136G-S141G-K303T-R307H | ++++++ | IN VIVO 2 |
| L200E-V74P-R197L-H211R-C43S-Y81R-T91S-N133S-S141G-Y260H-K303T-G311C | ++++++ | IN VIVO 2 |
| L200E-V74P-R197L-H211R-C43S-Y81R-T91S-Q99K-L135C-R136G-S141G-K303T | ++++++ | IN VIVO 2 |
| L200E-V74P-R197L-H211R-G44D-Q99K-S141G-Y260H-R307H | ++++++ | IN VIVO 2 |
| L200E-V74P-R197L-H211R-G44D-R80A-N133S-L135C-S141G-K303T | ++++++ | IN VIVO 2 |
| L200E-V74P-R197L-H211R-G44D-R80A-Q99K-L135C-S141G-K303T | ++++++ | IN VIVO 2 |
| L200E-V74P-R197L-H211R-G44D-R80A-S141G-Y260H-R307H | ++++++ | IN VIVO 2 |
| L200E-V74P-R197L-H211R-G44D-R80A-T91S-Q99K-N133S-L135C-S141G-Y260H-R307H | ++++++ | IN VIVO 2 |
| L200E-V74P-R197L-H211R-G44D-R80A-Y81R-N133S-S141G-R307H | ++++++ | IN VIVO 2 |
| L200E-V74P-R197L-H211R-G44D-R80A-Y81R-T91S-N133S-L135C-S141A-A180T-Y260H-K303T | ++++++ | IN VIVO 2 |
| L200E-V74P-R197L-H211R-G44D-S73P-Y81R-T91S-Q99K-L135C-S141G-Y260H-K303T | ++++++ | IN VIVO 2 |
| L200E-V74P-R197L-H211R-G44D-T91S-K123R-L135C-S141G-Y260H-K303T | ++++++ | IN VIVO 2 |
| L200E-V74P-R197L-H211R-G44D-T91S-N133S-S141G-Y260H-K303T | ++++++ | IN VIVO 2 |
| L200E-V74P-R197L-H211R-G44D-T91S-Q99K-A118T-N133S-L135C-S141G-S175T-Y260H-K303T | ++++++ | IN VIVO 2 |
| L200E-V74P-R197L-H211R-G44D-T91S-Q99K-L135C-S141G-K303T | ++++++ | IN VIVO 2 |
| L200E-V74P-R197L-H211R-G44D-T91S-Q99K-L135C-S141G-Y260H-K303T-R307H | ++++++ | IN VIVO 2 |
| L200E-V74P-R197L-H211R-G44D-T91S-Q99K-L135C-S141G-Y260H-R307H | ++++++ | IN VIVO 2 |
| L200E-V74P-R197L-H211R-G44D-T91S-S141G-R307H | ++++++ | IN VIVO 2 |
| L200E-V74P-R197L-H211R-G44D-Y81R-Q99K-L135C-S141G-Y260H-K303T-R307H | ++++++ | IN VIVO 2 |
| L200E-V74P-R197L-H211R-G44D-Y81R-Q99K-N133S-R136G-S141G-Y260H-K303T | ++++++ | IN VIVO 2 |
| L200E-V74P-R197L-H211R-G44D-Y81R-S141G-R307H | ++++++ | IN VIVO 2 |
| L200E-V74P-R197L-H211R-G44D-Y81R-S141G-Y260H | ++++++ | IN VIVO 2 |
| L200E-V74P-R197L-H211R-G44D-Y81R-S141G-Y260H-R307H | ++++++ | IN VIVO 2 |
| L200E-V74P-R197L-H211R-G44D-Y81R-T91S-L135C-S141G-K303T-R307H | ++++++ | IN VIVO 2 |
| L200E-V74P-R197L-H211R-G44D-Y81R-T91S-L135C-S141G-Y260H-K303T | ++++++ | IN VIVO 2 |
| L200E-V74P-R197L-H211R-G44D-Y81R-T91S-Q99K-N133S-S141G-Y260H | ++++++ | IN VIVO 2 |
| L200E-V74P-R197L-H211R-G44D-Y81R-T91S-Q99K-S141G-Y260H-K303T | ++++++ | IN VIVO 2 |
| L200E-V74P-R197L-H211R-G90P-T91S-L135C-S141A | ++++++ | IN VIVO 2 |
| L200E-V74P-R197L-H211R-G90S-T91S-S141A-R307H | ++++++ | IN VIVO 2 |
| L200E-V74P-R197L-H211R-L135C-A137S-R307H | ++++++ | IN VIVO 2 |
| L200E-V74P-R197L-H211R-L135C-A137S-S141A-R307H | ++++++ | IN VIVO 2 |
| L200E-V74P-R197L-H211R-L135C-R136G-S141A | ++++++ | IN VIVO 2 |
| L200E-V74P-R197L-H211R-L135C-S141A | ++++++ | IN VIVO 2 |
| L200E-V74P-R197L-H211R-L135C-S141A-A289V | ++++++ | IN VIVO 2 |
| L200E-V74P-R197L-H211R-L135C-S141A-R307H | ++++++ | IN VIVO 2 |
| L200E-V74P-R197L-H211R-R80A-D127N-L135C-S141A | ++++++ | IN VIVO 2 |
| L200E-V74P-R197L-H211R-R80A-G90S-T91G-L135C-S141A | ++++++ | IN VIVO 2 |
| L200E-V74P-R197L-H211R-R80A-G90S-T91S-S141A-R307H | ++++++ | IN VIVO 2 |
| L200E-V74P-R197L-H211R-R80A-L135C-R136G-S141A | ++++++ | IN VIVO 2 |
| L200E-V74P-R197L-H211R-R80A-T91G-A137S-S141A-R307H | ++++++ | IN VIVO 2 |
| L200E-V74P-R197L-H211R-R80A-Y81R-A137P-S141A-R307H | ++++++ | IN VIVO 2 |
| L200E-V74P-R197L-H211R-R80A-Y81R-L135C-S141A | ++++++ | IN VIVO 2 |
| L200E-V74P-R197L-H211R-R80A-Y81R-L135C-S141A-R307H | ++++++ | IN VIVO 2 |
| L200E-V74P-R197L-H211R-S141A | ++++++ | IN VIVO 2 |

TABLE 1-continued

List of *Thermoplasma acidophilum* mevalonate kinase variants presenting an increase in 3-phosphonoxyisovalerate production from 3-hydroxyisovalerate

| Mutations | Activity relative to the wild-type enzyme | Screening Assay used |
|---|---|---|
| L200E-V74P-R197L-H211R-S73P-R80A-L135C-R307H | ++++++ | IN VIVO 2 |
| L200E-V74P-R197L-H211R-S73P-R80A-T91S-L135C-A137S-S141A-R307H | ++++++ | IN VIVO 2 |
| L200E-V74P-R197L-H211R-S73P-R80A-Y81R-L135C-S141A-R307H | ++++++ | IN VIVO 2 |
| L200E-V74P-R197L-H211R-S73P-T91G-L135C-S141A-R307H | ++++++ | IN VIVO 2 |
| L200E-V74P-R197L-H211R-S73P-T91S-L135C-A137P-S141A-R307H | ++++++ | IN VIVO 2 |
| L200E-V74P-R197L-H211R-T91G-L135C-R136G-S141A | ++++++ | IN VIVO 2 |
| L200E-V74P-R197L-H211R-T91P-L135C-A137S-S141A | ++++++ | IN VIVO 2 |
| L200E-V74P-R197L-H211R-T91P-L135C-S141A-R307H | ++++++ | IN VIVO 2 |
| L200E-V74P-R197L-H211R-T91S-A137P-S141A | ++++++ | IN VIVO 2 |
| L200E-V74P-R197L-H211R-Y81R-A137P-S141A | ++++++ | IN VIVO 2 |
| L200E-V74P-R197L-H211R-Y81R-S141A | ++++++ | IN VIVO 2 |
| L200E-V74P-R197L-H211R-Y81R-S141A-R307H | ++++++ | IN VIVO 2 |
| L200E-V74P-R197L-H211R-Y81R-T91G-L135C-A137S | ++++++ | IN VIVO 2 |
| L200E-V74P-R197L-H211R-Y81R-T91G-S141A | ++++++ | IN VIVO 2 |
| L200E-V74P-R197L-H211R-Y81R-T91S-S141A | ++++++ | IN VIVO 2 |
| L200E-V77P-L135C-H211R-V74P-R80A-Y81G-R197L-S141G | ++++++ | IN VIVO 2 |
| L200E-V77P-L135C-H211R-V74P-R80A-Y81R-R197L-S141A-C43S-Q99K-N133S-K303T | ++++++ | IN VIVO 2 |
| L200E-V77P-L135C-H211R-V74P-R80A-Y81R-R197L-S141A-C43S-Q99K-N133S-Y260H-K303T | ++++++ | IN VIVO 2 |
| L200E-V77P-L135C-H211R-V74P-R80A-Y81R-R197L-S141A-G44D-N133S-K303T | ++++++ | IN VIVO 2 |
| L200E-V77P-L135C-H211R-V74P-R80A-Y81R-R197L-S141A-K303T | ++++++ | IN VIVO 2 |
| L200E-V77P-L135C-H211R-V74P-R80A-Y81R-R197L-S141G-A178N | ++++++ | IN VIVO 2 |
| L200E-V77P-L135C-H211R-V74P-R80A-Y81R-R197L-S141G-A180C | ++++++ | IN VIVO 2 |
| L200E-V77P-L135C-H211R-V74P-R80A-Y81R-R197L-S141G-A180E | ++++++ | IN VIVO 2 |
| L200E-V77P-L135C-H211R-V74P-R80A-Y81R-R197L-S141G-A180G | ++++++ | IN VIVO 2 |
| L200E-V77P-L135C-H211R-V74P-R80A-Y81R-R197L-S141G-A180L | ++++++ | IN VIVO 2 |
| L200E-V77P-L135C-H211R-V74P-R80A-Y81R-R197L-S141G-A180R | ++++++ | IN VIVO 2 |
| L200E-V77P-L135C-H211R-V74P-R80A-Y81R-R197L-S141G-A54R | ++++++ | IN VIVO 2 |
| L200E-V77P-L135C-H211R-V74P-R80A-Y81R-R197L-S141G-C43G | ++++++ | IN VIVO 2 |
| L200E-V77P-L135C-H211R-V74P-R80A-Y81R-R197L-S141G-C43S-G44D-N133S-K303T | ++++++ | IN VIVO 2 |
| L200E-V77P-L135C-H211R-V74P-R80A-Y81R-R197L-S141G-C43S-N133S-K303T | ++++++ | IN VIVO 2 |
| L200E-V77P-L135C-H211R-V74P-R80A-Y81R-R197L-S141G-C43S-N133S-Y260H-K303T | ++++++ | IN VIVO 2 |
| L200E-V77P-L135C-H211R-V74P-R80A-Y81R-R197L-S141G-C43S-Q99K-N133S-K303T | ++++++ | IN VIVO 2 |
| L200E-V77P-L135C-H211R-V74P-R80A-Y81R-R197L-S141G-C43S-Q99K-N133S-Y260H-K303T-S141G | ++++++ | IN VIVO 2 |
| L200E-V77P-L135C-H211R-V74P-R80A-Y81R-R197L-S141G-D189E | ++++++ | IN VIVO 2 |
| L200E-V77P-L135C-H211R-V74P-R80A-Y81R-R197L-S141G-D189S | ++++++ | IN VIVO 2 |
| L200E-V77P-L135C-H211R-V74P-R80A-Y81R-R197L-S141G-D70L | ++++++ | IN VIVO 2 |
| L200E-V77P-L135C-H211R-V74P-R80A-Y81R-R197L-S141G-E217M | ++++++ | IN VIVO 2 |
| L200E-V77P-L135C-H211R-V74P-R80A-Y81R-R197L-S141G-E296T | ++++++ | IN VIVO 2 |
| L200E-V77P-L135C-H211R-V74P-R80A-Y81R-R197L-S141G-E56S | ++++++ | IN VIVO 2 |
| L200E-V77P-L135C-H211R-V74P-R80A-Y81R-R197L-S141G-G311P | ++++++ | IN VIVO 2 |
| L200E-V77P-L135C-H211R-V74P-R80A-Y81R-R197L-S141G-G311Q | ++++++ | IN VIVO 2 |
| L200E-V77P-L135C-H211R-V74P-R80A-Y81R-R197L-S141G-G44D-N133S-K303T | ++++++ | IN VIVO 2 |

TABLE 1-continued

List of *Thermoplasma acidophilum* mevalonate kinase variants presenting an increase in 3-phosphonoxyisovalerate production from 3-hydroxyisovalerate

| Mutations | Activity relative to the wild-type enzyme | Screening Assay used |
|---|---|---|
| L200E-V77P-L135C-H211R-V74P-R80A-Y81R-R197L-S141G-G64E | ++++++ | IN VIVO 2 |
| L200E-V77P-L135C-H211R-V74P-R80A-Y81R-R197L-S141G-G7L | ++++++ | IN VIVO 2 |
| L200E-V77P-L135C-H211R-V74P-R80A-Y81R-R197L-S141G-G7Q | ++++++ | IN VIVO 2 |
| L200E-V77P-L135C-H211R-V74P-R80A-Y81R-R197L-S141G-I119V | ++++++ | IN VIVO 2 |
| L200E-V77P-L135C-H211R-V74P-R80A-Y81R-R197L-S141G-I52F-P202S | ++++++ | IN VIVO 2 |
| L200E-V77P-L135C-H211R-V74P-R80A-Y81R-R197L-S141G-I52L | ++++++ | IN VIVO 2 |
| L200E-V77P-L135C-H211R-V74P-R80A-Y81R-R197L-S141G-I52M | ++++++ | IN VIVO 2 |
| L200E-V77P-L135C-H211R-V74P-R80A-Y81R-R197L-S141G-I60H | ++++++ | IN VIVO 2 |
| L200E-V77P-L135C-H211R-V74P-R80A-Y81R-R197L-S141G-I60W | ++++++ | IN VIVO 2 |
| L200E-V77P-L135C-H211R-V74P-R80A-Y81R-R197L-S141G-N133S | ++++++ | IN VIVO 2 |
| L200E-V77P-L135C-H211R-V74P-R80A-Y81R-R197L-S141G-N133S-K303T | ++++++ | IN VIVO 2 |
| L200E-V77P-L135C-H211R-V74P-R80A-Y81R-R197L-S141G-N133S-Y260H-K303T | ++++++ | IN VIVO 2 |
| L200E-V77P-L135C-H211R-V74P-R80A-Y81R-R197L-S141G-N248T | ++++++ | IN VIVO 2 |
| L200E-V77P-L135C-H211R-V74P-R80A-Y81R-R197L-S141G-N71G | ++++++ | IN VIVO 2 |
| L200E-V77P-L135C-H211R-V74P-R80A-Y81R-R197L-S141G-P187E | ++++++ | IN VIVO 2 |
| L200E-V77P-L135C-H211R-V74P-R80A-Y81R-R197L-S141G-P187G | ++++++ | IN VIVO 2 |
| L200E-V77P-L135C-H211R-V74P-R80A-Y81R-R197L-S141G-P187M | ++++++ | IN VIVO 2 |
| L200E-V77P-L135C-H211R-V74P-R80A-Y81R-R197L-S141G-P187V | ++++++ | IN VIVO 2 |
| L200E-V77P-L135C-H211R-V74P-R80A-Y81R-R197L-S141G-R315T | ++++++ | IN VIVO 2 |
| L200E-V77P-L135C-H211R-V74P-R80A-Y81R-R197L-S141G-R75G | ++++++ | IN VIVO 2 |
| L200E-V77P-L135C-H211R-V74P-R80A-Y81R-R197L-S141G-S172M | ++++++ | IN VIVO 2 |
| L200E-V77P-L135C-H211R-V74P-R80A-Y81R-R197L-S141G-S5A | ++++++ | IN VIVO 2 |
| L200E-V77P-L135C-H211R-V74P-R80A-Y81R-R197L-S141G-S5F | ++++++ | IN VIVO 2 |
| L200E-V77P-L135C-H211R-V74P-R80A-Y81R-R197L-S141G-S8C | ++++++ | IN VIVO 2 |
| L200E-V77P-L135C-H211R-V74P-R80A-Y81R-R197L-S141G-S98T | ++++++ | IN VIVO 2 |
| L200E-V77P-L135C-H211R-V74P-R80A-Y81R-R197L-S141G-T9H | ++++++ | IN VIVO 2 |
| L200E-V77P-L135C-H211R-V74P-R80A-Y81R-R197L-S141G-V17I | ++++++ | IN VIVO 2 |
| L200E-V77P-L135C-H211R-V74P-R80A-Y81R-R197L-S141G-V17L-P25S | ++++++ | IN VIVO 2 |
| L200E-V77P-L135C-H211R-V74P-R80A-Y81R-R197L-S141G-W313L | ++++++ | IN VIVO 2 |
| L200E-V77P-L135C-H211R-V74P-R80A-Y81R-R197L-S141G-W313S | ++++++ | IN VIVO 2 |
| L200E-V77P-L135C-H211R-V74P-R80A-Y81R-R197L-S141G-W313V | ++++++ | IN VIVO 2 |
| L200E-V77P-L135C-H211R-V74P-R80A-Y81R-R197L-S141G-Y174F | ++++++ | IN VIVO 2 |
| L200E-V77P-L135C-H211R-V74P-R80A-Y81R-R197L-S141G-Y260F | ++++++ | IN VIVO 2 |
| L200E-V74P-V77P-R80A-Y81R-L135C-S141G-R197L-H211R-G7L-I52L-S172M-W313V | +++++++ | IN VIVO 3 |
| L200E-V74P-V77P-R80A-Y81R-L135C-S141G-R197L-H211R-V17L-P25S-D70L-S98T-G311P | +++++++ | IN VIVO 3 |
| L200E-V74P-V77P-R80A-Y81R-L135C-S141G-R197L-H211R-G7Q-V17L-I60H | +++++++ | IN VIVO 3 |

TABLE 1-continued

List of *Thermoplasma acidophilum* mevalonate kinase variants presenting an increase in 3-phosphonoxyisovalerate production from 3-hydroxyisovalerate

| Mutations | Activity relative to the wild-type enzyme | Screening Assay used |
|---|---|---|
| L200E-V74P-V77P-R80A-Y81R-L135C-S141G-R197L-H211R-G7Q-I52L | +++++++ | IN VIVO 3 |
| L200E-V74P-V77P-R80A-Y81R-L135C-S141G-R197L-H211R-G7Q-I52L-W313L | +++++++ | IN VIVO 3 |
| L200E-V74P-V77P-R80A-Y81R-L135C-S141G-R197L-H211R-D70L-S98T-R315H | +++++++ | IN VIVO 3 |
| L200E-V74P-V77P-R80A-Y81R-L135C-S141G-R197L-H211R-D70L-S98T-G311P | +++++++ | IN VIVO 3 |
| L200E-V74P-V77P-R80A-Y81R-L135C-S141G-R197L-H211R-G7Q-I52L-S172M-W313L | +++++++ | IN VIVO 3 |
| L200E-V74P-V77P-R80A-Y81R-L135C-S141G-R197L-H211R-I52L-S98T-Y174F-G311P | +++++++ | IN VIVO 3 |
| L200E-V74P-V77P-R80A-Y81R-L135C-S141G-R197L-H211R-P25S-I60H-G311P | +++++++ | IN VIVO 3 |
| L200E-V74P-V77P-R80A-Y81R-L135C-S141G-R197L-H211R-S5A-G7Q-V17L-P25S-D70L-Y174F | +++++++ | IN VIVO 3 |
| L200E-V74P-V77P-R80A-Y81R-L135C-S141G-R197L-H211R-V17L-P25S-D70L-S98T | +++++++ | IN VIVO 3 |
| L200E-V74P-V77P-R80A-Y81R-L135C-S141G-R197L-H211R-P25S-S98T-G311P | +++++++ | IN VIVO 3 |
| L200E-V74P-V77P-R80A-Y81R-L135C-S141G-R197L-H211R-I60H | +++++++ | IN VIVO 3 |
| L200E-V74P-V77P-R80A-Y81R-L135C-S141G-R197L-H211R-P25S-I52L-S98T-Y174F | +++++++ | IN VIVO 3 |
| L200E-V74P-V77P-R80A-Y81R-L135C-S141G-R197L-H211R-G7Q-P25S-I52L | +++++++ | IN VIVO 3 |
| L200E-V74P-V77P-R80A-Y81R-L135C-S141G-R197L-H211R-P25S-I52L-S98T-G311P | +++++++ | IN VIVO 3 |
| L200E-V74P-V77P-R80A-Y81R-L135C-S141G-R197L-H211R-P25S-I119V-W313S | +++++++ | IN VIVO 3 |
| L200E-V74P-V77P-R80A-Y81R-L135C-S141G-R197L-H211R-P25S-S98T | +++++++ | IN VIVO 3 |
| L200E-V74P-V77P-R80A-Y81R-L135C-S141G-R197L-H211R-G7Q-P25S-I60H | +++++++ | IN VIVO 3 |
| L200E-V74P-V77P-R80A-Y81R-L135C-S141G-R197L-H211R-P25S-I60H | +++++++ | IN VIVO 3 |
| L200E-V74P-V77P-R80A-Y81R-L135C-S141G-R197L-H211R-I52L-S98T | +++++++ | IN VIVO 3 |
| L200E-V74P-V77P-R80A-Y81R-L135C-S141G-R197L-H211R-S98T-I119V-Y174F | +++++++ | IN VIVO 3 |
| L200E-V74P-V77P-R80A-Y81R-L135C-S141G-R197L-H211R-V17L-R51H | +++++++ | IN VIVO 3 |
| L200E-V74P-V77P-R80A-Y81R-L135C-S141G-R197L-H211R-S98T-G311P-W313S | +++++++ | IN VIVO 3 |
| L200E-V74P-V77P-R80A-Y81R-L135C-S141G-R197L-H211R-I52L | +++++++ | IN VIVO 3 |
| L200E-C43S-V74P-R80A-Y81R-N133S-S141G-R197L-H211R-K303T-R307H-G7Q-I52L | +++++++ | IN VIVO 3 |
| L200E-C43S-V74P-R80A-Y81R-N133S-S141G-R197L-H211R-K303T-R307H-G7L-I52L-S172M-W313V-N186M | +++++++ | IN VIVO 3 |
| L200E-C43S-V74P-R80A-Y81R-N133S-S141G-R197L-H211R-K303T-R307H-A203S-K205R-K206R | +++++++ | IN VIVO 3 |
| L200E-C43S-V74P-R80A-Y81R-N133S-S141G-R197L-H211R-K303T-R307H-I14V-V16I-V17I | +++++++ | IN VIVO 3 |
| L200E-C43S-V74P-R80A-Y81R-N133S-S141G-R197L-H211R-K303T-R307H-R315H-R316H-E318D | +++++++ | IN VIVO 3 |

TABLE 2

List of mutations involved in the variants of *Thermoplasma acidophilum* mevalonate kinase with increased activity

| Mutant | Wild-Type Amino Acid | Sequence Number | Mutation |
|---|---|---|---|
| Y3H | Y | 3 | H |
| S5A | S | 5 | A |
| S5F | S | 5 | F |
| I6L | I | 6 | L |
| G7L | G | 7 | L |

TABLE 2-continued

List of mutations involved in the variants of *Thermoplasma acidophilum* mevalonate kinase with increased activity

| Mutant | Wild-Type Amino Acid | Sequence Number | Mutation |
|---|---|---|---|
| G7Q | G | 7 | Q |
| G7V | G | 7 | V |
| S8C | S | 8 | C |
| S8T | S | 8 | T |
| T9H | T | 9 | H |

TABLE 2-continued

List of mutations involved in the variants of *Thermoplasma acidophilum* mevalonate kinase with increased activity

| Mutant | Wild-Type Amino Acid | Sequence Number | Mutation |
|---|---|---|---|
| I14V | I | 14 | V |
| V16I | V | 16 | I |
| V17I | V | 17 | I |
| V17L | V | 17 | L |
| A23T | A | 23 | T |
| N24D | N | 24 | D |
| P25L | P | 25 | L |
| P25R | P | 25 | R |
| P25S | P | 25 | S |
| V26F | V | 26 | F |
| H32D | H | 32 | D |
| C43G | C | 43 | G |
| C43S | C | 43 | S |
| G44D | G | 44 | D |
| S45I | S | 45 | I |
| I46V | I | 46 | V |
| E49D | E | 49 | D |
| E49G | E | 49 | G |
| E49S | E | 49 | S |
| R51H | R | 51 | H |
| I52F | I | 52 | F |
| I52L | I | 52 | L |
| I52M | I | 52 | M |
| A54R | A | 54 | R |
| E56S | E | 56 | S |
| H59R | H | 59 | R |
| I60H | I | 60 | H |
| I60W | I | 60 | W |
| G64E | G | 64 | E |
| T65D | T | 65 | D |
| T65E | T | 65 | E |
| S67C | S | 67 | C |
| S67N | S | 67 | N |
| D70L | D | 70 | L |
| D70V | D | 70 | V |
| N71G | N | 71 | G |
| N71I | N | 71 | I |
| S73P | S | 73 | P |
| V74P | V | 74 | P |
| R75G | R | 75 | G |
| R76P | R | 76 | P |
| V77P | V | 77 | P |
| R80A | R | 80 | A |
| R80T | R | 80 | T |
| Y81E | Y | 81 | E |
| Y81G | Y | 81 | G |
| Y81Q | Y | 81 | Q |
| Y81R | Y | 81 | R |
| Y81T | Y | 81 | T |
| S82D | S | 82 | D |
| S83N | S | 83 | N |
| A88T | A | 88 | T |
| F89G | F | 89 | G |
| F89S | F | 89 | S |
| G90P | G | 90 | P |
| G90S | G | 90 | S |
| T91G | T | 91 | G |
| T91P | T | 91 | P |
| T91S | T | 91 | S |
| K92T | K | 92 | T |
| T93I | T | 93 | I |
| V94A | V | 94 | A |
| V94S | V | 94 | S |
| S98T | S | 98 | T |
| Q99K | Q | 99 | K |
| I115V | I | 115 | V |
| A118T | A | 118 | T |
| I119V | I | 119 | V |
| G121A | G | 121 | A |
| K123N | K | 123 | N |
| K123R | K | 123 | R |
| D127N | D | 127 | N |
| N133S | N | 133 | S |
| L135C | L | 135 | C |
| R136G | R | 136 | G |

TABLE 2-continued

List of mutations involved in the variants of *Thermoplasma acidophilum* mevalonate kinase with increased activity

| Mutant | Wild-Type Amino Acid | Sequence Number | Mutation |
|---|---|---|---|
| A137E | A | 137 | E |
| A137P | A | 137 | P |
| A137S | A | 137 | S |
| S141A | S | 141 | A |
| S141G | S | 141 | G |
| F147L | F | 147 | L |
| F158S | F | 158 | S |
| A160V | A | 160 | V |
| S172M | S | 172 | M |
| Y174F | Y | 174 | F |
| S175T | S | 175 | T |
| A178N | A | 178 | N |
| A180C | A | 180 | C |
| A180E | A | 180 | E |
| A180G | A | 180 | G |
| A180L | A | 180 | L |
| A180R | A | 180 | R |
| A180T | A | 180 | T |
| Y183D | Y | 183 | D |
| Q184P | Q | 184 | P |
| N186M | N | 186 | M |
| P187E | P | 187 | E |
| P187G | P | 187 | G |
| P187M | P | 187 | M |
| P187V | P | 187 | V |
| D189E | D | 189 | E |
| D189S | D | 189 | S |
| R197C | R | 197 | C |
| R197K | R | 197 | K |
| R197L | R | 197 | L |
| L200E | L | 200 | E |
| L200T | L | 200 | T |
| P202S | P | 202 | S |
| A203S | A | 203 | S |
| K205I | K | 205 | I |
| K205R | K | 205 | R |
| K206R | K | 206 | R |
| A208T | A | 208 | T |
| H211K | H | 211 | K |
| H211R | H | 211 | R |
| E217M | E | 217 | M |
| S240G | S | 240 | G |
| N248T | N | 248 | T |
| E252K | E | 252 | K |
| E252S | E | 252 | S |
| K256R | K | 256 | R |
| S259N | S | 259 | N |
| Y260F | Y | 260 | F |
| Y260H | Y | 260 | H |
| E285C | E | 285 | C |
| A289V | A | 289 | V |
| I295N | I | 295 | N |
| E296T | E | 296 | T |
| K302R | K | 302 | R |
| K303T | K | 303 | T |
| R307H | R | 307 | H |
| G311C | G | 311 | C |
| G311P | G | 311 | P |
| G311Q | G | 311 | Q |
| W313L | W | 313 | L |
| W313R | W | 313 | R |
| W313S | W | 313 | S |
| W313T | W | 313 | T |
| W313V | W | 313 | V |
| W313Y | W | 313 | Y |
| R315H | R | 315 | H |
| R315K | R | 315 | K |
| R315T | R | 315 | T |
| R316H | R | 316 | H |
| E318D | E | 318 | D |

TABLE 3

| List of the positions modified in the variants of *Thermoplasma acidophilum* mevalonate kinase with increased activity | | |
|---|---|---|
| Position | Wild-Type Amino Acid | Mutations |
| 3 | Y | H |
| 5 | S | A, F |
| 6 | I | L |
| 7 | G | L, Q, V |
| 8 | S | C, T |
| 9 | T | H |
| 14 | I | V |
| 16 | V | I |
| 17 | V | I, L |
| 23 | A | T |
| 24 | N | D |
| 25 | P | L, R, S |
| 26 | V | F |
| 32 | H | D |
| 43 | C | G, S |
| 44 | G | D |
| 45 | S | I |
| 46 | I | V |
| 49 | E | D, G, S |
| 51 | R | H |
| 52 | I | F, L, M |
| 54 | A | R |
| 56 | E | S |
| 59 | H | R |
| 60 | I | H, W |
| 64 | G | E |
| 65 | T | D, E |
| 67 | S | C, N |
| 70 | D | L, V |
| 71 | N | G, I |
| 73 | S | P |
| 74 | V | P |
| 75 | R | G |
| 76 | R | P |
| 77 | V | P |
| 80 | R | A, T |
| 81 | Y | E, G, Q, R, T |
| 82 | S | D |
| 83 | S | N |
| 88 | A | T |
| 89 | F | G, S |
| 90 | G | P, S |
| 91 | T | G, P, S |
| 92 | K | T |
| 93 | T | I |
| 94 | V | A, S |
| 98 | S | T |
| 99 | Q | K |
| 115 | I | V |
| 118 | A | T |
| 119 | I | V |
| 121 | G | A |
| 123 | K | N, R |
| 127 | D | N |
| 133 | N | S |
| 135 | L | C |
| 136 | R | G |
| 137 | A | E, P, S |
| 141 | S | A, G |
| 147 | F | L |
| 158 | F | S |
| 160 | A | V |
| 172 | S | M |
| 174 | Y | F |
| 175 | S | T |
| 178 | A | N |
| 180 | A | C, E, G, L, R, T |
| 183 | Y | D |
| 184 | Q | P |
| 186 | N | M |
| 187 | P | E, G, M, V |
| 189 | D | E, S |
| 197 | R | C, K, L |
| 200 | L | E, T |
| 202 | P | S |

TABLE 3-continued

| List of the positions modified in the variants of *Thermoplasma acidophilum* mevalonate kinase with increased activity | | |
|---|---|---|
| Position | Wild-Type Amino Acid | Mutations |
| 203 | A | S |
| 205 | K | I, R |
| 206 | K | R |
| 208 | A | T |
| 211 | H | K, R |
| 217 | E | M |
| 240 | S | G |
| 248 | N | T |
| 252 | E | K, S |
| 256 | K | R |
| 259 | S | N |
| 260 | Y | F, H |
| 285 | E | C |
| 289 | A | V |
| 295 | I | N |
| 296 | E | T |
| 302 | K | R |
| 303 | K | T |
| 307 | R | H |
| 311 | G | C, P, Q |
| 313 | W | L, R, S, T, V, Y |
| 315 | R | H, K, T |
| 316 | R | H |
| 318 | E | D |

Example 5

In Vitro Characterization of *Thermoplasma acidophilum* Mevalonate Kinase Variants with Increased Activity for the Reaction of Conversion of 3-hydroxyisovalerate into 3-phosphonoxyisovalerate The activity of *Thermoplasma acidophilum* mevalonate kinase variants for the conversion of 3-hydroxyisovalerate (HIV) into 3-phosphonoxyisovalerate (PIV) can be assessed by an enzymatic in vitro assay based on purified proteins and on the detection of PIV by High-Performance Liquid Chromatography (HPLC).

The *Thermoplasma acidophilum* mevalonate kinase enzyme variants were cloned in the pET 25b vector (Novagen). A stretch of 6 histidine codons was inserted after the methionine initiation codon to provide an affinity tag for purification and a unique cleavage site for the TEV protease (ENLYFQG) in order to remove the affinity tag from the purified protein. Competent *E. coli* BL21 (DE3) cells (Novagen) were transformed with these vectors according to the heat shock procedure and plated out onto LB-agar plates supplemented with the appropriate antibiotic. Cells were grown overnight at 30° C. until individual colonies reach the desired size. Single colonies were then picked and individually transferred into 5 mL of liquid LB medium supplemented with the appropriate antibiotic. Cell growth is carried out with shaking for 16 hours at 30° C. The LB cultures were used to inoculate 1 L of of auto-induction medium (Studier F W, Prat. Exp. Pur. 41, (2005), 207-234) supplemented with the appropriate antibiotic and grown in a shaking incubator set at 170 rpm and 85% humidity for 6 h at 37° C. and protein expression was continued at 28° C. overnight (approximately 16 h). The cells were collected by centrifugation at 4° C., 4000 rpm for 20 min and the pellets were frozen at −80° C. The pellets were thawed on ice and resuspended in 40 ml of BugBuster (Millipore) and four microliter of lysonase (Novagen) was added. Cells were incubated 10 minutes at room temperature and then returned to ice for 20 minutes. The bacterial extracts were then clarified by centrifugation at 4° C., 10,000 rpm for 30 min. The clarified bacterial lysates were loaded on Protino Ni-IDA columns (Macherey-Nagel) allowing adsorption of 6-His tagged proteins. Columns were washed and the enzymes of interest were eluted with 6 mL of the supplied elution buffer. Eluates were then concentrated and desalted by centrifugation, washing and resuspension in 1 mL of 100 mM Tris/HCl pH 7.5, 50 mM NaCl, 5% glycerol. Protein concentrations were quantified using a Nanodrop 1000 (ThermoScientific). Cleavage of the affinity tag was then performed by adding 100 U TEV protease (Invitrogen) per 1 μg of purified protein and incubated overnight at 4° C. The uncleaved proteins were separated by affinity chromatography using an Akta Purifier and a HisTrap HP 5 mL column (GE Healthcare Life Sciences) using standard protocol. The cleaved proteins were collected in the flow-through and concentrated by centrifugation, washing and resuspension in 100 μL of 50 mM Tris/HCl pH 7.5 on Amicon Ultra 4 mL with a 10 kDa cut-off (Merck Millipore). Protein concentrations were quantified using a Nanodrop 1000 (Thermo-Scientific).

The enzymatic assay for quantifying the conversion of HIV into PIV was carried out at 37° C. in a 50 mM Tris/HCl pH 7.5 buffer with 10 mM MgCl2, 10 mM NaCl, 20 mM ATP, 0.1 mg/mL enzyme and different concentration of HIV ranging from 0 to 128 mM. After 30 min, the reaction was stopped by incubating at 80° C. for 5 min. The rate of PIV production was quantified by HPLC analyses performed using a 1260 Infinity LC System (Agilent), equipped with a refractometer detector and a column heating module. 2 μL sample was separated on a Polaris 150 column (150×2 mm, 5 μm particle size, column temperature 30° C.). The mobile phase consisted of 16 mM sulphuric acid in water with 1% methanol and was run with a flow rate of 1.5 mL/min. Retention time of HIV and PIV was 4.8 and 3.5 min, respectively. Commercial HIV and PIV were used as reference. From the rate of PIV production, and using the Michaelis-Menten approximation, the enzyme catalytic efficiency can then be computed.

The invention claimed is:

1. A variant of an 3-hydroxyisovalerate (HIV) kinase showing an improved activity in converting 3-hydroxyisovalerate (HIV) into 3-phosphonoxyisovalerate (PIV) over the corresponding HIV kinase from which it is derived, wherein the HIV kinase variant has at least 80% sequence identity to SEQ ID NO:1, and in which the HIV kinase variant comprises one or more substitutions, deletions or insertions at one or more of the positions corresponding to positions 3, 5, 6, 7, 8, 9, 14, 16, 17, 23, 24, 25, 26, 32, 43, 44, 45, 46, 49, 51, 52, 54, 56, 59, 60, 64, 65, 67, 70, 71, 73, 74, 75, 76, 77, 80, 81, 82, 83, 88, 89, 90, 91, 92, 93, 94, 98, 99, 115, 118, 119, 121, 123, 127, 133, 135, 136, 137, 141, 147, 158, 160, 172, 174, 175, 178, 180, 183, 184, 186, 187, 189, 197, 202, 203, 205, 206, 208, 211, 217, 240, 248, 252, 256, 259, 260, 285, 289, 295, 296, 302, 303, 307, 311, 313, 315, 316 and 318 in the amino acid sequence of SEQ ID NO:1.

2. The HIV kinase variant of claim 1, wherein said HIV kinase variant has at least 90% sequence identity to SEQ ID NO:1.

3. The HIV kinase variant of claim 1, wherein (1) the amino acid residue at position 3 in the amino acid sequence of SEQ ID NO:1 is deleted or substituted with histidine; and/or (2) the amino acid residue at position 5 in the amino acid sequence of SEQ ID NO:1 is deleted or substituted with alanine or phenylalanine; and/or (3) the amino acid residue at position 6 in the amino acid sequence of SEQ ID NO:1 is deleted or substituted with leucine; and/or (4) the amino acid residue at position 7 in the amino acid sequence of SEQ ID NO:1 is deleted or substituted with leucine, glutamine or valine; and/or (5) the amino acid residue at position 8 in the amino acid sequence of SEQ ID NO:1 is deleted or substituted with cysteine or threonine; and/or (6) the amino acid residue at position 9 in the amino acid sequence of SEQ ID NO:1 is deleted or substituted with histidine; and/or (7) the amino acid residue at position 14 in the amino acid sequence of SEQ ID NO:1 is deleted or substituted with valine; and/or (8) the amino acid residue at position 16 in the amino acid sequence of SEQ ID NO:1 is deleted or substituted with isoleucine; and/or (9) the amino acid residue at position 17 in the amino acid sequence of SEQ ID NO:1 is deleted or substituted with isoleucine or leucine; and/or

(10) the amino acid residue at position 23 in the amino acid sequence of SEQ ID NO:1 is deleted or substituted with threonine; and/or

(11) the amino acid residue at position 24 in the amino acid sequence of SEQ ID NO:1 is deleted or substituted with aspartic acid; and/or

(12) the amino acid residue at position 25 in the amino acid sequence of SEQ ID NO:1 is deleted or substituted with leucine, arginine or serine; and/or

(13) the amino acid residue at position 26 in the amino acid sequence of SEQ ID NO:1 is deleted or substituted with phenylalanine; and/or

(14) the amino acid residue at position 32in the amino acid sequence of SEQ ID NO:1 is deleted or substituted with aspartic acid; and/or

(15) the amino acid residue at position 43 in the amino acid sequence of SEQ ID NO:1 is deleted or substituted with glycine or serine; and/or

(16) the amino acid residue at position 44 in the amino acid sequence of SEQ ID NO:1 is deleted or substituted with aspartic acid; and/or

(16) the amino acid residue at position 45 in the amino acid sequence of SEQ ID NO:1 is deleted or substituted with isoleucine; and/or

(18) the amino acid residue at position 46 in the amino acid sequence of SEQ ID NO:1 is deleted or substituted with valine; and/or

(19) the amino acid residue at position 49 in the amino acid sequence of SEQ ID NO:1 is deleted or substituted with aspartic acid, glycine or serine; and/or

(20) the amino acid residue at position 51in the amino acid sequence of SEQ ID NO:1 is deleted or substituted with histidine; and/or

(21) the amino acid residue at position 52 in the amino acid sequence of SEQ ID NO:1 is deleted or substituted with phenylalanine, leucine or methionine; and/or

(22) the amino acid residue at position 54 in the amino acid sequence of SEQ ID NO:1 is deleted or substituted with arginine; and/or

(23) the amino acid residue at position 56 in the amino acid sequence of SEQ ID NO:1 is deleted or substituted with serine; and/or

(24) the amino acid residue at position 59 in the amino acid sequence of SEQ ID NO:1 is deleted or substituted with arginine; and/or

(25) the amino acid residue at position 60 in the amino acid sequence of SEQ ID NO:1 is deleted or substituted with histidine or tryptophan; and/or

(26) the amino acid residue at position 64 in the amino acid sequence of SEQ ID NO:1 is deleted or substituted with glutamic acid; and/or

(27) the amino acid residue at position 65 in the amino acid sequence of SEQ ID NO:1 is deleted or substituted with aspartic acid or glutamic acid; and/or

(28) the amino acid residue at position 67 in the amino acid sequence of SEQ ID NO:1 is deleted or substituted with cysteine or asparagine; and/or

(29) the amino acid residue at position 70 in the amino acid sequence of SEQ ID NO:1 is deleted or substituted with leucine or valine; and/or

(30) the amino acid residue at position 71 in the amino acid sequence of SEQ ID NO:1 is deleted or substituted with glycine or isoleucine; and/or

(31) the amino acid residue at position 73 in the amino acid sequence of SEQ ID NO:1 is deleted or substituted with proline; and/or

(32) the amino acid residue at position 74 in the amino acid sequence of SEQ ID NO:1 is deleted or substituted with proline; and/or

(33) the amino acid residue at position 75 in the amino acid sequence of SEQ ID NO:1 is deleted or substituted with glycine; and/or

(34) the amino acid residue at position 76 in the amino acid sequence of SEQ ID NO:1 is deleted or substituted with proline; and/or

(35) the amino acid residue at position 77 in the amino acid sequence of SEQ ID NO:1 is deleted or substituted with proline; and/or

(36) the amino acid residue at position 80 in the amino acid sequence of SEQ ID NO:1 is deleted or substituted with alanine or threonine; and/or

(37) the amino acid residue at position 81 in the amino acid sequence of SEQ ID NO:1 is deleted or substituted with glutamic acid, glycine, glutamine, arginine or threonine; and/or

(38) the amino acid residue at position 82 in the amino acid sequence of SEQ ID NO:1 is deleted or substituted with aspartic acid; and/or

(39) the amino acid residue at position 83 in the amino acid sequence of SEQ ID NO:1 is deleted or substituted with asparagine; and/or

(40) the amino acid residue at position 88 in the amino acid sequence of SEQ ID NO:1 is deleted or substituted with threonine; and/or

(41) the amino acid residue at position 89 in the amino acid sequence of SEQ ID NO:1 is deleted or substituted with glycine or serine; and/or

(42) the amino acid residue at position 90 in the amino acid sequence of SEQ ID NO:1 is deleted or substituted with proline or serine; and/or

(43) the amino acid residue at position 91 in the amino acid sequence of SEQ ID NO:1 is deleted or substituted with glycine, proline or serine; and/or

(44) the amino acid residue at position 92 in the amino acid sequence of SEQ ID NO:1 is deleted or substituted with threonine; and/or

(45) the amino acid residue at position 93 in the amino acid sequence of SEQ ID NO:1 is deleted or substituted with isoleucine; and/or

(46) the amino acid residue at position 94 in the amino acid sequence of SEQ ID NO:1 is deleted or substituted with alanine or serine; and/or

(47) the amino acid residue at position 98 in the amino acid sequence of SEQ ID NO:1 is deleted or substituted with threonine; and/or

(48) the amino acid residue at position 99 in the amino acid sequence of SEQ ID NO:1 is deleted or substituted with lysine; and/or

(49) the amino acid residue at position 115 in the amino acid sequence of SEQ ID NO:1 is deleted or substituted with valine; and/or

(50) the amino acid residue at position 118 in the amino acid sequence of SEQ ID NO:1 is deleted or substituted with threonine; and/or

(51) the amino acid residue at position 119 in the amino acid sequence of SEQ ID NO:1 is deleted or substituted with valine; and/or

(52) the amino acid residue at position 121 in the amino acid sequence of SEQ ID NO:1 is deleted or substituted with alanine; and/or

(53) the amino acid residue at position 123 in the amino acid sequence of SEQ ID NO:1 is deleted or substituted with arginine or asparagine; and/or

(54) the amino acid residue at position 127 in the amino acid sequence of SEQ ID NO:1 is deleted or substituted with asparagine; and/or

(55) the amino acid residue at position 133 in the amino acid sequence of SEQ ID NO:1 is deleted or substituted with serine; and/or

(56) the amino acid residue at position 135 in the amino acid sequence of SEQ ID NO:1 is deleted or substituted with cysteine; and/or

(57) the amino acid residue at position 136 in the amino acid sequence of SEQ ID NO:1 is deleted or substituted with glycine; and/or

(58) the amino acid residue at position 137 in the amino acid sequence of SEQ ID NO:1 is deleted or substituted with glutamic acid, proline or serine; and/or

(59) the amino acid residue at position 141 in the amino acid sequence of SEQ ID NO:1 is deleted or substituted with alanine or glycine; and/or

(60) the amino acid residue at position 147 in the amino acid sequence of SEQ ID NO:1 is deleted or substituted with leucine; and/or

(61) the amino acid residue at position 158 in the amino acid sequence of SEQ ID NO:1 is deleted or substituted with serine; and/or

(62) the amino acid residue at position 160 in the amino acid sequence of SEQ ID NO:1 is deleted or substituted with valine; and/or

(63) the amino acid residue at position 172 in the amino acid sequence of SEQ ID NO:1 is deleted or substituted with methionine; and/or

(64) the amino acid residue at position 174 in the amino acid sequence of SEQ ID NO:1 is deleted or substituted with phenylalanine; and/or

(65) the amino acid residue at position 175 in the amino acid sequence of SEQ ID NO:1 is deleted or substituted with threonine; and/or

(66) the amino acid residue at position 178 in the amino acid sequence of SEQ ID NO:1 is deleted or substituted with asparagine; and/or

(67) the amino acid residue at position 180 in the amino acid sequence of SEQ ID NO:1 is deleted or substituted with cysteine, glutamic acid, glycine, leucine, arginine or threonine; and/or

(68) the amino acid residue at position 183 in the amino acid sequence of SEQ ID NO:1 is deleted or substituted with proline; and/or

(70) the amino acid residue at position 186 in the amino acid sequence of SEQ ID NO:1 is deleted or substituted with methionine; and/or

(71) the amino acid residue at position 187 in the amino acid sequence of SEQ ID NO:1 is deleted or substituted with glutamic acid, glycine, methionine or valine; and/or

(72) the amino acid residue at position 189 in the amino acid sequence of SEQ ID NO:1 is deleted or substituted with glutamic acid or serine; and/or

(73) the amino acid residue at position 197 in the amino acid sequence of SEQ ID NO:1 is deleted or substituted with cysteine, lysine or leucine; and/or

(74) the amino acid residue at position 202 in the amino acid sequence of SEQ ID NO:1 is deleted or substituted with serine; and/or

(75) the amino acid residue at position 203 in the amino acid sequence of SEQ ID NO:1 is deleted or substituted with serine; and/or

(76) the amino acid residue at position 205 in the amino acid sequence of SEQ ID NO:1 is deleted or substituted with isoleucine or arginine; and/or

(77) the amino acid residue at position 206 in the amino acid sequence of SEQ ID NO:1 is deleted or substituted with arginine; and/or

(78) the amino acid residue at position 208 in the amino acid sequence of SEQ ID NO:1 is deleted or substituted with threonine; and/or

(79) the amino acid residue at position 211 in the amino acid sequence of SEQ ID NO:1 is deleted or substituted with lysine or arginine; and/or

(80) the amino acid residue at position 217 in the amino acid sequence of SEQ ID NO:1 is deleted or substituted with methionine; and/or

(81) the amino acid residue at position 240 in the amino acid sequence of SEQ ID NO:1 is deleted or substituted with glycine; and/or

(82) the amino acid residue at position 248 in the amino acid sequence of SEQ ID NO:1 is deleted or substituted with threonine; and/or

(83) the amino acid residue at position 252 in the amino acid sequence of SEQ ID NO:1 is deleted or substituted with lysine or serine; and/or

(84) the amino acid residue at position 256 in the amino acid sequence of SEQ ID NO:1 is deleted or substituted with arginine; and/or

(85) the amino acid residue at position 259 in the amino acid sequence of SEQ ID NO:1 is deleted or substituted with asparagine; and/or

(86) the amino acid residue at position 260 in the amino acid sequence of SEQ ID NO:1 is deleted or substituted with phenylalanine or histidine; and/or

(87) the amino acid residue at position 285 in the amino acid sequence of SEQ ID NO:1 is deleted or substituted with cysteine; and/or

(88) the amino acid residue at position 289 in the amino acid sequence of SEQ ID NO:1 is deleted or substituted with valine; and/or

(89) the amino acid residue at position 295 in the amino acid sequence of SEQ ID NO:1 is deleted or substituted with asparagine; and/or

(90) the amino acid residue at position 296 in the amino acid sequence of SEQ ID NO:1 is deleted or substituted with threonine; and/or

(91) the amino acid residue at position 302 in the amino acid sequence of SEQ ID NO:1 is deleted or substituted with arginine; and/or

(92) the amino acid residue at position 303 in the amino acid sequence of SEQ ID NO:1 is deleted or substituted with threonine; and/or

(93) the amino acid residue at position 307 in the amino acid sequence of SEQ ID NO:1 is deleted or substituted with histidine; and/or

(94) the amino acid residue at position 311 in the amino acid sequence of SEQ ID NO:1 is deleted or substituted with cysteine, proline or glutamine; and/or

(95) the amino acid residue at position 313 in the amino acid sequence of SEQ ID NO:1 is deleted or substituted with leucine, arginine, serine, threonine, valine or tyrosine; and/or

(96) the amino acid residue at position 315 in the amino acid sequence of SEQ ID NO:1 is deleted or substituted with histidine, lysine or threonine; and/or

(97) the amino acid residue at position 316 in the amino acid sequence of SEQ ID NO:1 is deleted or substituted with histidine; and/or

(98) the amino acid residue at position 318 in the amino acid sequence of SEQ ID NO:1 is deleted or substituted with aspartic acid.

4. The HIV kinase variant of claim 1, wherein the HIV kinase variant further comprises at least one deletion, substitution and/or insertion at position 200 in the amino acid sequence of SEQ ID NO:1 or at a position corresponding to this position from which the HIV kinase variant is derived.

5. The HIV kinase variant of claim 4, wherein said HIV kinase variant has at least 90% sequence identity to SEQ ID NO:1.

6. A nucleic acid molecule encoding the HIV kinase variant of claim 1.

7. A vector comprising the nucleic acid molecule of claim 6.

8. An isolated host cell comprising the vector of claim 7.

9. A method for producing PIV from HIV by employing HIV with the HIV kinase variant of claim 1.

10. A method for producing isobutene (IBN) from HIV comprising the method of claim 9 and further the step of converting the thus produced PIV into IBN by a dephosphorylation/decarboxylation reaction.

11. The method according to claim 9, further comprising providing the HIV by the enzymatic conversion of acetone into said HIV.

12. The method of claim 9, wherein the enzymatic conversion is carried out in vitro.

13. A composition comprising a variant of an HIV kinase of claim 1.

14. The method of claim 9, wherein the enzymatic conversion is carried out in an isolated host cell.

15. A composition comprising the nucleic acid molecule of claim 6.

16. A composition comprising the vector of claim 7.

17. A composition comprising the isolated host cell of claim 8.

18. The HIV kinase variant of claim 2, wherein the HIV kinase variant further comprises at least one deletion, substitution and/or insertion at position 200 in the amino acid sequence of SEQ ID NO:1.

19. The HIV kinase variant of claim 3, wherein the HIV kinase variant further comprises at least one deletion, substitution and/or insertion at position 200 in the amino acid sequence of SEQ ID NO:1.

* * * * *

UNITED STATES PATENT AND TRADEMARK OFFICE

CERTIFICATE OF CORRECTION

PATENT NO. : 10,407,669 B2
APPLICATION NO. : 15/748034
DATED : September 10, 2019
INVENTOR(S) : Sabine Mazaleyrat et al.

It is certified that error appears in the above-identified patent and that said Letters Patent is hereby corrected as shown below:

In the Claims

Column 102, Lines 13, 14, and 15 should read:
-- the amino acid residue at position 32 in the amino acid sequence of SEQ ID NO: 1 is deleted or substituted with aspartic acid; and/or --

Signed and Sealed this
Third Day of March, 2020

Andrei Iancu
*Director of the United States Patent and Trademark Office*